United States Patent
Komiyama et al.

(10) Patent No.: US 6,221,359 B1
(45) Date of Patent: Apr. 24, 2001

(54) HEMOPOIETIC STEM CELL MULTIPLIER

(75) Inventors: Atsushi Komiyama; Tatsutoshi Nakahata; Tetsuo Kubo, all of Matsumoto; Ryuhei Tanaka, Tsu; Genji Kawano; Tetsuo Sudo, both of Kamakura; Emiko Sano; Katsuaki Kojima, both of Yokohama, all of (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 08/030,410

(22) PCT Filed: Jul. 24, 1992

(86) PCT No.: PCT/JP92/00949

§ 371 Date: May 21, 1993

§ 102(e) Date: May 21, 1993

(87) PCT Pub. No.: WO93/03061

PCT Pub. Date: Feb. 18, 1993

(30) Foreign Application Priority Data

Jul. 26, 1991 (JP) .................................................. 3-187470
Jul. 26, 1991 (JP) .................................................. 3-187481

(51) Int. Cl.$^7$ .................................................. C12K 14/00
(52) U.S. Cl. ..................................... 424/198.1; 424/198.1
(58) Field of Search ..................................... 530/350, 351, 530/399; 514/2; 536/23.51; 424/85.2; 435/69.4, 240.1, 320.1

(56) References Cited

U.S. PATENT DOCUMENTS 5,004,805 * 4/1991 Gohda et al. .
5,328,836 * 7/1994 Shima et al. ........................ 435/69.4
5,362,716 * 11/1994 Kmiecik .

OTHER PUBLICATIONS

Iyer et al 1990. Cell Growth Diff. 1:87.*
Ihle et al. 1984 Curr Top Microbiol Immunol 113:86.*
Seki et al. 1990, Biochem. Biophys. Res. Commun. 172(1):321–327.*
Rubin et al. 1991 P.N.A.S. 88:415–419.*
Bottaro et al 1991 Science 251 802–804.*
Fletcher et al. 1990. J. Cell. Biochem. Suppl. 0(14pt E):90.*
Ikebuchi et al. (1987) "Interleukin 6 Enhancement of Interleukin 3–Dependent Proliferation of Multipotential Hemopoietic Progenitors", *Proc. Natl. Acad. Sci. USA 84*, 9035–9039.
Kodama et al. (1982) "A New Preadipose Cell Line Derived from Newborn Mouse Calvaria can Promote the Proliferation of Pluripotent Hemopoietic Stem Cell In Vitro", *Journal of Cellular Physiology 112*, 89–95.
Nakamura et al. (1989) "Molecular Cloning and Expression of Human Hepatocyte Growth Factor", *Nature 342*, 440–443.
Nakamura et al. (1984) "Partial Purification and Characterization of Hepatocyte Growth Factor from Serum of Hepatectomized Rats", *Biochemical and Biophysical Research Communications 122*, 1450–1459.

* cited by examiner

Primary Examiner—Karen Cochrane Carlson
(74) Attorney, Agent, or Firm—Scully, Scott, Murphy & Presser

(57) ABSTRACT

A hemopoietic stem cell augmenting agent in which at least one type of hepatocyte growth factor is contained as an active component is provided. The hepatocyte growth factor has an augmenting activity on undifferentiated pluripotent hemopoietic stem cells and is useful as a hemopoietic stem cell augmenting agent for treatment of bone marrow suppression and for treatment of bone marrow malfunctions and furthermore is useful for in vitro growth of peripheral blood stem cells and bone marrow stem cells. Furthermore, a hepatocyte growth factor derived from human normal fibroblasts which is considered to be a type of hepatocyte growth factor can be obtained by genetic recombination techniques, and said factor is also useful as a hemopoietic stem cells augmenting agent.

9 Claims, 14 Drawing Sheets

```
ATG TGG GTG ACC AAA CTC CTG CCA GCC CTG CTG CTG CAG CAT GTC CTC      48
Met Trp Val Thr Lys Leu Leu Pro Ala Leu Leu Leu Gln His Val Leu
1               5                   10                  15

CTG CAT CTC CTC CTG CTC CCC ATC GCC ATC CCC TAT GCA GAG GGA CAA      96
Leu His Leu Leu Leu Leu Pro Ile Ala Ile Pro Tyr Ala Glu Gly Gln
                20                  25                  30

ACG AAA AGA AGA AAT ACA ATT CAT GAA TTC AAA AAA TCA GCA AAG ACT     144
Arg Lys Arg Arg Asn Thr Ile His Glu Phe Lys Lys Ser Ala Lys Thr
            35                  40                  45

ACC CTA ATC AAA ATA GAT CCA GCA CTG AAG ATA AAA ACC AAA AAA GTG     192
Thr Leu Ile Lys Ile Asp Pro Ala Leu Lys Ile Lys Thr Lys Lys Val
        50                  55                  60

AAT ACT GCA GAC CAA TGT GCT AAT AGA TGT ACT AGG AAT AAA GGA CTT     240
Asn Thr Ala Asp Gln Cys Ala Asn Arg Cys Thr Arg Asn Lys Gly Leu
65                  70                  75                  80

CCA TTC ACT TGC AAG GCT TTT GTT TTT GAT AAA GCA AGA AAA CAA TGC     288
Pro Phe Thr Cys Lys Ala Phe Val Phe Asp Lys Ala Arg Lys Gln Cys
                85                  90                  95

CTC TGG TTC CCC TTC AAT AGC ATG TCA AGT GGA GTG AAA AAA GAA TTT     336
Leu Trp Phe Pro Phe Asn Ser Met Ser Ser Gly Val Lys Lys Glu Phe
                    100                 105                 110

GCC CAT GAA TTT GAC CTC TAT GAA AAC AAA GAC TAC ATT AGA AAC TGC     384
Gly His Glu Phe Asp Leu Tyr Glu Asn Lys Asp Tyr Ile Arg Asn Cys
            115                 120                 125

ATC ATT GGT AAA GGA CGC AGC TAC AAG GGA ACA GTA TCT ATC ACT AAG     432
Ile Ile Gly Lys Gly Arg Ser Tyr Lys Gly Thr Val Ser Ile Thr Lys
        130                 135                 140
```

Figure 2A

```
AGT GGC ATC AAA TGT CAG CCC TGG AGT TCC ATG ATA CCA CAC GAA CAC      480
Ser Gly Ile Lys Cys Gln Pro Trp Ser Ser Met Ile Pro His Glu His
145             150             155             160

AGC TAT CGG GGT AAA GAC CTA CAG GAA AAC TAC TGT CGA AAT CCT CGA      528
Ser Tyr Arg Gly Lys Asp Leu Gln Glu Asn Tyr Cys Arg Asn Pro Arg
                165             170             175

GGG GAA GAA GGG GGA CCC TGG TGT TTC ACA AGC AAT CCA GAG GTA CGC      576
Gly Glu Glu Gly Gly Pro Trp Cys Phe Thr Ser Asn Pro Glu Val Arg
        180             185             190

TAC GAA GTC TGT GAC ATT CCT CAG TGT TCA GAA GTT GAA TGC ATG ACC      624
Tyr Glu Val Cys Asp Ile Pro Gln Cys Ser Glu Val Glu Cys Met Thr
            195             200             205

TGC AAT GGG GAG AGT TAT CGA GGT CTC ATG GAT CAT ACA GAA TCA GGC      672
Cys Asn Gly Glu Ser Tyr Arg Gly Leu Met Asp His Thr Glu Ser Gly
        210             215             220

AGG ATT TGT CAG CGC TGG GAT CAT CAG ACA CCA CAC CGG CAC AAA TTC      720
Arg Ile Cys Gln Arg Trp Asp His Gln Thr Pro His Arg His Lys Phe
225             230             235             240

TTG CCT GAA AGA TAT CCC GAC AAG GGC TTT GAT GAT AAT TAT TGC CGC      768
Leu Pro Glu Arg Tyr Pro Asp Lys Gly Phe Asp Asp Asn Tyr Cys Arg
                245             250             255

AAT CCC GAT GGC CAG CCG AGG CCA TGG TGC TAT ACT CTT GAC CCT CAC      816
Asn Pro Asp Gly Gln Pro Arg Pro Trp Cys Tyr Thr Leu Asp Pro His
        260             265             270

ACC CGC TGG GAG TAC TGT GCA ATT AAA ACA TGC GCT GAC AAT ACT ATG      864
Thr Arg Trp Glu Tyr Cys Ala Ile Lys Thr Cys Ala Asp Asn Thr Met
275             280             285
```

Figure 2B

```
AAT GAC ACT GAT GTT CCT TTG GAA ACA ACT GAA TGC ATC CAA GGT CAA    912
Asn Asp Thr Asp Val Pro Leu Glu Thr Thr Glu Cys Ile Gln Gly Gln
290             295             300

GGA GAA GGC TAC AGG GGC ACT GTC AAT ACC ATT TGG AAT GGA ATT CCA    960
Gly Glu Gly Tyr Arg Gly Thr Val Asn Thr Ile Trp Asn Gly Ile Pro
305             310             315             320

TGT CAG CGT TGG GAT TCT CAG TAT CCT CAC GAG CAT GAC ATG ACT CCT    1008
Cys Gln Arg Trp Asp Ser Gln Tyr Pro His Glu His Asp Met Thr Pro
                325             330             335

GAA AAT TTC AAG TGC AAG GAC CTA AGA GAA AAT TAC TGC CGA AAT CCA    1056
Glu Asn Phe Lys Cys Lys Asp Leu Arg Glu Asn Tyr Cys Arg Asn Pro
        340             345             350

GAT GGG TCT GAA TCA CCC TGG TGT TTT ACC ACT GAT CCA AAC ATC CGA    1104
Asp Gly Ser Glu Ser Pro Trp Cys Phe Thr Thr Asp Pro Asn Ile Arg
355             360             365

GTT GGC TAC TGC TCC CAA ATT CCA AAC TGT GAT ATG TCA CAT GGA CAA    1152
Val Gly Tyr Cys Ser Gln Ile Pro Asn Cys Asp Met Ser His Gly Gln
370             375             380

GAT TGT TAT CGT GGG AAT GGC AAA AAT TAT ATG GGC AAC TTA TCC CAA    1200
Asp Cys Tyr Arg Gly Asn Gly Lys Asn Tyr Met Gly Asn Leu Ser Gln
385             390             395             400

ACA AGA TCT GGA CTA ACG TGT TCA ATG TGG GAC AAG AAC ATG GAA GAC    1248
Thr Arg Ser Gly Leu Thr Cys Ser Met Trp Asp Lys Asn Met Glu Asp
            405             410             415

TTA CAC CGT CAT ATC TTC TGG GAA CCA GAT GCA AGT AAG CTG AAT GAG    1296
Leu His Arg His Ile Phe Trp Glu Pro Asp Ala Ser Lys Leu Asn Glu
            420             425             430
```

Figure 2C

```
AAT TAC TGC CGA AAT CCA GAT GAT GAT GCT CAT GGA CCC TGG TGC TAC    1344
Asn Tyr Cys Arg Asn Pro Asp Asp Asp Ala His Gly Pro Trp Cys Tyr
        435             440             445

ACG GGA AAT CCA CTC ATT CCT TGG GAT TAT TGC CCT ATT TCT CGT TGT    1392
Thr Gly Asn Pro Leu Ile Pro Trp Asp Tyr Cys Pro Ile Ser Arg Cys
        450             455             460

GAA GGT GAT ACC ACA CCT ACA ATA GTC AAT TTA GAC CAT CCC GTA ATA    1440
Glu Gly Asp Thr Thr Pro Thr Ile Val Asn Leu Asp His Pro Val Ile
    465             470             475             480

TCT TGT GCC AAA ACG AAA CAA CTG CGA GTT GTA AAT GGG ATT CCA ACA    1488
Ser Cys Ala Lys Thr Lys Gln Leu Arg Val Val Asn Gly Ile Pro Thr
        485             490             495

CGA ACA AAC GTA GGA TGG ATG GTT AGT TTG AGA TAC AGA AAT AAA CAT    1536
Arg Thr Asn Val Gly Trp Met Val Ser Leu Arg Tyr Arg Asn Lys His
        500             505             510

ATC TGC GGA GGA TCA TTG ATA AAG GAG AGT TGG GTT CTT ACT GCA CGA    1584
Ile Cys Gly Gly Ser Leu Ile Lys Glu Ser Trp Val Leu Thr Ala Arg
        515             520             525

CAG TGT TTC CCT TCT CGA GAC TTG AAA GAT TAT GAA GCT TGG CTT GGA    1632
Gln Cys Phe Pro Ser Arg Asp Leu Lys Asp Tyr Glu Ala Trp Leu Gly
        530             535             540

ATT CAT GAT GTC CAT GGA AGA GGA GAT GAG AAA TGC AAA CAG GTT CTC    1680
Ile His Asp Val His Gly Arg Gly Asp Glu Lys Cys Lys Gln Val Leu
    545             550             555             560

AAT GTT TCC CAG CTG GTA TAT GGC CCT GAA GGA TCA GAT CTG GTT TTA    1728
Asn Val Ser Gln Leu Val Tyr Gly Pro Glu Gly Ser Asp Leu Val Leu
        565             570             575
```

Figure 2D

```
ATG AAG CTT GCC ACG CCT CCT GTC CTG GAT GAT TTT GTT AGT ACG ATT    1776
Met Lys Leu Ala Arg Pro Ala Val Leu Asp Asp Phe Val Ser Thr Ile
        580             585             590

GAT TTA CCT AAT TAT GGA TGC ACA ATT CCT GAA AAG ACC AGT TGC AGT    1824
Asp Leu Pro Asn Tyr Gly Cys Thr Ile Pro Glu Lys Thr Ser Cys Ser
        595             600             605

GTT TAT GGC TGG GGC TAC ACT GGA TTG ATC AAC TAT GAT GGC CCA TTA    1872
Val Tyr Gly Trp Gly Tyr Thr Gly Leu Ile Asn Tyr Asp Gly Pro Leu
        610             615             620

CGA GTG GCA CAT CTC TAT ATA ATG GGA AAT GAG AAA TGC ACC CAG CAT    1920
Arg Val Ala His Leu Tyr Ile Met Gly Asn Glu Lys Cys Ser Gln His
625             630             635             640

CAT CGA GGG AAG GTG ACT CTG AAT GAG TCT GAA ATA TGT GCT GGG GCT    1968
His Arg Gly Lys Val Thr Leu Asn Glu Ser Glu Ile Cys Ala Gly Ala
        645             650             655

GAA AAG ATT GGA TCA GGA CCA TGT GAG GGG GAT TAT GGT GGC CCA CTT    2016
Glu Lys Ile Gly Ser Gly Pro Cys Glu Gly Asp Tyr Gly Gly Pro Leu  672
        660             665             670

GTT TGT GAG CAA CAT AAA ATG AGA ATG GTT CTT GGT GTC ATT GTT CCT    2064
Val Cys Glu Gln His Lys Met Arg Met Val Leu Gly Val Ile Val Pro
        675             680             685

GGT CGT GGA TGT GCC ATT CCA AAT CGT CCT GGT ATT TTT GTC CGA GTA    2112
Gly Arg Gly Cys Ala Ile Pro Asn Arg Pro Gly Ile Phe Val Arg Val
        690             695             700

GCA TAT TAT GCA AAA TGG ATA CAC AAA ATT ATT TTA ACA TAT AAG GTA    2160
Ala Tyr Tyr Ala Lys Trp Ile His Lys Ile Ile Leu Thr Tyr Lys Val
705             710             715             720
```

Figure 2E

E————————————————————————————————E
CCA CAG TCA TAG                                                    2172
Pro Gln Ser ***

Figure 2F

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Val Val Asn Gly Ile Pro Thr Xaa Thr Asn Ile Gly Xaa Met Val Lys
1               5                   10                  15
```

(2) INFORMATION FOR SEQ ID NO:2:

(i) SEQUENCE CHARACTERISTICS:
      (A) LENGTH: 2172 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..2169

(xi) SEQUENCE DESCRIPTION: SEQ ID NO:2:

```
ATG TGG GTG ACC AAA CTC CTG CCA GCC CTG CTG CTG CAG CAT GTC CTC      48
Met Trp Val Thr Lys Leu Leu Pro Ala Leu Leu Leu Gln His Val Leu
 1               5                  10                  15

CTG CAT CTC CTC CTG CTC CCC ATC GCC ATC CCC TAT GCA GAG GGA CAA      96
Leu His Leu Leu Leu Leu Pro Ile Ala Ile Pro Tyr Ala Glu Gly Gln
                20                  25                  30

AGG AAA AGA AGA AAT ACA ATT CAT GAA TTC AAA AAA TCA GCA AAG ACT     144
Arg Lys Arg Arg Asn Thr Ile His Glu Phe Lys Lys Ser Ala Lys Thr
            35                  40                  45

ACC CTA ATC AAA ATA GAT CCA GCA CTG AAG ATA AAA ACC AAA AAA GTG     192
Thr Leu Ile Lys Ile Asp Pro Ala Leu Lys Ile Lys Thr Lys Lys Val
        50                  55                  60

AAT ACT GCA GAC CAA TGT GCT AAT AGA TGT ACT AGG AAT AAA GGA CTT    240
Asn Thr Ala Asp Gln Cys Ala Asn Arg Cys Thr Arg Asn Lys Gly Leu
 65                  70                  75                  80

CCA TTC ACT TGC AAG GCT TTT GTT TTT GAT AAA GCA AGA AAA CAA TGC     288
Pro Phe Thr Cys Lys Ala Phe Val Phe Asp Lys Ala Arg Lys Gln Cys
                85                  90                  95

CTC TGG TTC CCC TTC AAT AGC ATG TCA AGT GGA GTG AAA AAA GAA TTT     336
Leu Trp Phe Pro Phe Asn Ser Met Ser Ser Gly Val Lys Lys Glu Phe
                100                 105                 110

GGC CAT GAA TTT GAC CTC TAT GAA AAC AAA GAC TAC ATT AGA AAC TGC     384
Gly His Glu Phe Asp Leu Tyr Glu Asn Lys Asp Tyr Ile Arg Asn Cys
            115                 120                 125

ATC ATT GGT AAA GGA CGC AGC TAC AAG GGA ACA GTA TCT ATC ACT AAG     432
Ile Ile Gly Lys Gly Arg Ser Tyr Lys Gly Thr Val Ser Ile Thr Lys
        130                 135                 140

AGT GGC ATC AAA TGT CAG CCC TGG AGT TCC ATG ATA CCA CAC GAA CAC     480
Ser Gly Ile Lys Cys Gln Pro Trp Ser Ser Met Ile Pro His Glu His
145                 150                 155                 160
```

```
AGC TAT CGG GGT AAA GAC CTA CAG GAA AAC TAC TGT CGA AAT CCT CGA      528
Ser Tyr Arg Gly Lys Asp Leu Gln Glu Asn Tyr Cys Arg Asn Pro Arg
            165                 170                 175

GGG GAA GAA GGG GGA CCC TGG TGT TTC ACA AGC AAT CCA GAG GTA CGC      576
Gly Glu Glu Gly Gly Pro Trp Cys Phe Thr Ser Asn Pro Glu Val Arg
            180                 185                 190

TAC GAA GTC TGT GAC ATT CCT CAG TGT TCA GAA GTT GAA TGC ATG ACC      624
Tyr Glu Val Cys Asp Ile Pro Gln Cys Ser Glu Val Glu Cys Met Thr
            195                 200                 205

TGC AAT GGG GAG AGT TAT CGA GGT CTC ATG GAT CAT ACA GAA TCA GGC      672
Cys Asn Gly Glu Ser Tyr Arg Gly Leu Met Asp His Thr Glu Ser Gly
210                 215                 220

AGG ATT TGT CAG CGC TGG GAT CAT CAG ACA CCA CAC CGG CAC AAA TTC      720
Arg Ile Cys Gln Arg Trp Asp His Gln Thr Pro His Arg His Lys Phe
225                 230                 235                 240

TTG CCT GAA AGA TAT CCC GAC AAG GGC TTT GAT GAT AAT TAT TGC CGC      768
Leu Pro Glu Arg Tyr Pro Asp Lys Gly Phe Asp Asp Asn Tyr Cys Arg
            245                 250                 255

AAT CCC GAT GGC CAG CCG AGG CCA TGG TGC TAT ACT CTT GAC CCT CAC      816
Asn Pro Asp Gly Gln Pro Arg Pro Trp Cys Tyr Thr Leu Asp Pro His
            260                 265                 270

ACC CGC TGG GAG TAC TGT GCA ATT AAA ACA TGC GCT GAC AAT ACT ATG      864
Thr Arg Trp Glu Tyr Cys Ala Ile Lys Thr Cys Ala Asp Asn Thr Met
            275                 280                 285

AAT GAC ACT GAT GTT CCT TTG GAA ACA ACT GAA TGC ATC CAA GGT CAA      912
Asn Asp Thr Asp Val Pro Leu Glu Thr Thr Glu Cys Ile Gln Gly Gln
            290                 295                 300

GGA GAA GGC TAC AGG GGC ACT GTC AAT ACC ATT TGG AAT GGA ATT CCA      960
Gly Glu Gly Tyr Arg Gly Thr Val Asn Thr Ile Trp Asn Gly Ile Pro
305                 310                 315                 320

TGT CAG CGT TGG GAT TCT CAG TAT CCT CAC GAG CAT GAC ATG ACT CCT     1008
Cys Gln Arg Trp Asp Ser Gln Tyr Pro His Glu His Asp Met Thr Pro
            325                 330                 335

GAA AAT TTC AAG TGC AAG GAC CTA CGA GAA AAT TAC TGC CGA AAT CCA     1056
Glu Asn Phe Lys Cys Lys Asp Leu Arg Glu Asn Tyr Cys Arg Asn Pro
            340                 345                 350

GAT GGG TCT GAA TCA CCC TGG TGT TTT ACC ACT GAT CCA AAC ATC CGA     1104
Asp Gly Ser Glu Ser Pro Trp Cys Phe Thr Thr Asp Pro Asn Ile Arg
            355                 360                 365

GTT GGC TAC TGC TCC CAA ATT CCA AAC TGT GAT ATG TCA CAT GGA CAA     1152
Val Gly Tyr Cys Ser Gln Ile Pro Asn Cys Asp Met Ser His Gly Gln
            370                 375                 380

GAT TGT TAT CGT GGG AAT GGC AAA AAT TAT ATG GGC AAC TTA TCC CAA     1200
Asp Cys Tyr Arg Gly Asn Gly Lys Asn Tyr Met Gly Asn Leu Ser Gln
385                 390                 395                 400

ACA AGA TCT GGA CTA ACG TGT TCA ATG TGG GAC AAG AAC ATG GAA GAC     1248
Thr Arg Ser Gly Leu Thr Cys Ser Met Trp Asp Lys Asn Met Glu Asp
            405                 410                 415

TTA CAC CGT CAT ATC TTC TGG GAA CCA GAT GCA AGT AAG CTG AAT GAG     1296
Leu His Arg His Ile Phe Trp Glu Pro Asp Ala Ser Lys Leu Asn Glu
            420                 425                 430

AAT TAC TGC CGA AAT CCA GAT GAT GAT GCT CAT GGA CCC TGG TGC TAC     1344
Asn Tyr Cys Arg Asn Pro Asp Asp Asp Ala His Gly Pro Trp Cys Tyr
            435                 440                 445

ACG GGA AAT CCA CTC ATT CCT TGG GAT TAT TGC CCT ATT TCT CGT TGT     1392
Thr Gly Asn Pro Leu Ile Pro Trp Asp Tyr Cys Pro Ile Ser Arg Cys
450                 455                 460

GAA GGT GAT ACC ACA CCT ACA ATA GTC AAT TTA GAC CAT CCC GTA ATA     1440
Glu Gly Asp Thr Thr Pro Thr Ile Val Asn Leu Asp His Pro Val Ile
```

```
465                470                475                480
TCT TGT GCC AAA ACG AAA CAA CTG CGA GTT GTA AAT GGG ATT CCA ACA          1488
Ser Cys Ala Lys Thr Lys Gln Leu Arg Val Val Asn Gly Ile Pro Thr
                485                490                495

CGA ACA AAC GTA GGA TGG ATG GTT AGT TTG AGA TAC AGA AAT AAA CAT          1536
Arg Thr Asn Val Gly Trp Met Val Ser Leu Arg Tyr Arg Asn Lys His
                500                505                510

ATC TGC GGA GGA TCA TTG ATA AAG GAG AGT TGG GTT CTT ACT GCA CGA          1584
Ile Cys Gly Gly Ser Leu Ile Lys Glu Ser Trp Val Leu Thr Ala Arg
                515                520                525

CAG TGT TTC CCT TCT CGA GAC TTG AAA GAT TAT GAA GCT TGG CTT GGA          1632
Gln Cys Phe Pro Ser Arg Asp Leu Lys Asp Tyr Glu Ala Trp Leu Gly
                530                535                540

ATT CAT GAT GTC CAT GGA AGA GGA GAT GAG AAA TGC AAA CAG GTT CTC          1680
Ile His Asp Val His Gly Arg Gly Asp Glu Lys Cys Lys Gln Val Leu
545                550                555                560

AAT GTT TCC CAG CTG GTA TAT GGC CCT GAA GGA TCA GAT CTG GTT TTA          1728
Asn Val Ser Gln Leu Val Tyr Gly Pro Glu Gly Ser Asp Leu Val Leu
                565                570                575

ATG AAG CTT GCC AGG CCT GCT GTC CTG GAT GAT TTT GTT AGT ACG ATT          1776
Met Lys Leu Ala Arg Pro Ala Val Leu Asp Asp Phe Val Ser Thr Ile
                580                585                590

GAT TTA CCT AAT TAT GGA TGC ACA ATT CCT GAA AAG ACC AGT TGC AGT          1824
Asp Leu Pro Asn Tyr Gly Cys Thr Ile Pro Glu Lys Thr Ser Cys Ser
                595                600                605

GTT TAT GGC TGG GGC TAC ACT GGA TTG ATC AAC TAT GAT GGC CCA TTA          1872
Val Tyr Gly Trp Gly Tyr Thr Gly Leu Ile Asn Tyr Asp Gly Pro Leu
                610                615                620

CGA GTG GCA CAT CTC TAT ATA ATG GGA AAT GAG AAA TGC AGC CAG CAT          1920
Arg Val Ala His Leu Tyr Ile Met Gly Asn Glu Lys Cys Ser Gln His
625                630                635                640

CAT CGA GGG AAG GTG ACT CTG AAT GAG TCT GAA ATA TGT GCT GGG GCT          1968
His Arg Gly Lys Val Thr Leu Asn Glu Ser Glu Ile Cys Ala Gly Ala
                645                650                655

GAA AAG ATT GGA TCA GGA CCA TGT GAG GGG GAT TAT GGT GGC CCA CTT          2016
Glu Lys Ile Gly Ser Gly Pro Cys Glu Gly Asp Tyr Gly Gly Pro Leu
                660                665                670

GTT TGT GAG CAA CAT AAA ATG AGA ATG GTT CTT GGT GTC ATT GTT CCT          2064
Val Cys Glu Gln His Lys Met Arg Met Val Leu Gly Val Ile Val Pro
                675                680                685

GGT CGT GGA TGT GCC ATT CCA AAT CGT CCT GGT ATT TTT GTC CGA GTA          2112
Gly Arg Gly Cys Ala Ile Pro Asn Arg Pro Gly Ile Phe Val Arg Val
                690                695                700

GCA TAT TAT GCA AAA TGG ATA CAC AAA ATT ATT TTA ACA TAT AAG GTA          2160
Ala Tyr Tyr Ala Lys Trp Ile His Lys Ile Ile Leu Thr Tyr Lys Val
705                710                715                720

CCA CAG TCA TAG                                                          2172
Pro Gln Ser
```

(2) INFORMATION FOR SEQ ID NO:3:

(i) SEQUENCE CHARACTERISTICS:
        (A) LENGTH: 723 amino acids
        (B) TYPE: amino acid
        (D) TOPOLOGY: linear (ii) MOLECULE TYPE: protein (xi) SEQUENCE DESCRIPTION: SEQ ID NO:3:

```
Met Trp Val Thr Lys Leu Leu Pro Ala Leu Leu Leu Gln His Val Leu
1               5                   10                  15
```

-continued

```
Leu His Leu Leu Leu Pro Ile Ala Ile Pro Tyr Ala Glu Gly Gln
             20                  25                  30

Arg Lys Arg Arg Asn Thr Ile His Glu Phe Lys Lys Ser Ala Lys Thr
             35                  40                  45

Thr Leu Ile Lys Ile Asp Pro Ala Leu Lys Ile Lys Thr Lys Lys Val
             50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
             85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
            130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
            165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
            195                 200                 205

Cys Asn Gly Glu Ser Tyr Arg Gly Leu Met Asp His Thr Glu Ser Gly
            210                 215                 220

Arg Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
            245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
            275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
            325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
            355                 360                 365

Val Gly Tyr Cys Ser Gln Ile Pro Asn Cys Asp Met Ser His Gly Gln
            370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
            405                 410                 415

Leu His Arg His Ile Phe Trp Glu Pro Asp Ala Ser Lys Leu Asn Glu
                420                 425                 430
```

```
Asn Tyr Cys Arg Asn Pro Asp Asp Ala His Gly Pro Trp Cys Tyr
            435                 440                 445

Thr Gly Asn Pro Leu Ile Pro Trp Asp Tyr Cys Pro Ile Ser Arg Cys
        450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Val Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
        530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Pro Leu
610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
            645                 650                 655

Glu Lys Ile Gly Ser Gly Pro Cys Glu Gly Asp Tyr Gly Gly Pro Leu
        660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser (2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATGTGGGTGA CCAAAC                                                16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

-continued (ii) MOLECULE TYPE: DNA (genomic)

(xi) SEQUENCE DESCRIPTION: SEQ ID NO:5:

CTATGACTGT GGTACC                                                                                       16

HEMOPOIETIC STEM CELL MULTIPLIER

FIELD OF INVENTION

The present invention relates to a hemopoietic stem cell augmenting agent. In particular, the present invention relates to a hemopoietic stem cell augmenting agent which has an activity to augment undifferentiated pluripotent hemopoietic stem cells. According to the present invention, therapeutic agents to restore bone marrow growth after the use of anti-cancer agents or after bone marrow transplantation or therapeutic agents for bone marrow malfunctions such as hypoplastic anemia and osteomyelodysplasia syndrome can be provided. Furthermore, this hemopoietic factor having the hemopoietic stem cell augmenting activity can be used as a useful reagent or the like for in vitro proliferation of peripheral stem cells and bone marrow stem cells and furthermore as an analytical reagent or as an antigen for preparation of antibodies.

Furthermore, the present invention also relates to a novel protein which belongs to hepatocyte growth factors and has a hemopoietic stem cell augmenting activity.

BACKGROUND OF THE INVENTION

Recently, it has been found that in the differentiation of undifferentiated pluripotent hemopoietic stem cells to mature blood cells, a number of hemopoietic factors are mutually involved In various levels and thus a complicated hemopoietic network system is formed. Furthermore, most of the hemopoietic factors are being genetically cloned and several hemopoietic factors are being mass produced by genetic recombination techniques, and their clinical applications are in progress. On the other hand, although pluripotent hemopoietic stem cells are characterized by their self-replicating ability (growth), sufficient studies have not been done on the growth factors which affect the undifferentiated pluripotent hemopoietic stem cells in the bone marrow.

It is known that bone marrow stromal cells play a major role in the growth of the pluripotent hemopoietic stem cells and their differentiation into mature cells; some kind of fluid factors secreted by the stromal cells, or intercellular reactions or the like are thought to be involved in hemopoieses in the bone marrow.

For example, it is known that bone marrow stromal cell line MC3T3-G2/PA-6(PA-6) which is established from the calvaria of C57B1/6 newborn mouse supports the growth of mouse pluripotent hemopoietic stem cells (Kodama, H. et al., J. Cell. Physiol., 112, 89, 1982).

In recent years, a ligand for a c-kit protein, which is a tyrosine kinase receptor being expressed in pluripotent stem cells, has attracted attention as a factor involved in the growth of undifferentiated stem cells and great efforts have been made to substantiate the ligand; in 1990, three research groups succeeded in genetically cloning the ligand. They were reported as SCF (stem cell factor; K. M. Zsebo et al., Cell, 63, 195–201, 1990), MGF (mast cell growth factor; D. E. Williams et al., Cell, 63, 167–174, 1990) and KL (c-kit ligand; Huang et al., Cell, 63, 225–233, 1990).

At present, the mechanism of the action of the ligand is being studied using the c-kit ligand which is mass produced by genetic recombination techniques and studies to date are clarifying that this factor acts on the stem cells which are differentiated to a certain extent (Hayashi et al., Int. J. Hematology, Suppl. No. 1, p198, 1991).

Accordingly, it is now considered that aside from this protein, other factors exist which act on pluripotent hemopoietic stem cells which are differentiated to a lesser extent in the bone marrow.

The hemopoietic factors having the above-mentioned activities can be made into useful pharmaceuticals such as therapeutic agents to restore bone marrow growth after the use of anti-cancer agents or after bone marrow transplantation and therapeutic agents for bone marrow malfunctions such as hypoplastic anemia and osteomyelodysplasia syndrome.

Furthermore, the hemopoietic factors having the above-mentioned activities can be used as a useful reagent or the like for in vitro proliferation of peripheral stem cells and bone marrow stem cells and furthermore as an analytical reagent or as an antigen for preparation of antibodies.

DISCLOSURE OF THE INVENTION

It is an object of the present invention to provide a hemopoietic stem cell augmenting agent which contains at least one hepatocyte growth factor as an active component. In particular, an object of the present invention is to provide a hemopoietic stem cell augmenting agent which has an activity for proliferating undifferentiated pluripotent hemopoietic stem cells. This hemopoietic stem cell augmenting agent eventually promotes proliferation of osteoclasts, the progeny of hemopoietic stem cells, as well as various blood cells. This hemopoietic stem cell augmenting agent may contain interleukin 3 and/or interleukin 7 as an active component(s) in addition to at least one of the hepatocyte growth factors.

A further object of the present invention is to provide a novel protein which is a type of hepatocyte growth factor and has a hemopoietic stem cell augmenting activity. In particular, such protein can be obtained from a culture fluid of human normal fibroblasts or by genetic recombination techniques using human normal fibroblasts as a gene supply source. It is a particular object of the present invention to provide a recombinant human hepatocyte growth factor protein, which is one type of hepatocyte growth factor and has the amino acid sequence of SEQ ID NO: 2 shown in Sequence Listing or a substance which has equivalent effectiveness. The protein is derived from human normal fibroblasts and preferably from fibroblasts of the highest normality. The present invention also provides a DNA which is characterized in that it contains a nucleotide sequence encoding an amino acid sequence of a protein, which is a type of hepatocyte growth factor and has a hemopoietic stem cell augmenting activity, or a substance equivalent in terms of effectiveness; a recombinant expression vector in which said coding nucleotide sequence is so incorporated as to be expressed; a transformant which is obtained by the transformation of a host cell using the expression vector; and a process for the preparation of a recombinant human hepatocyte growth factor protein, which is one of hepatocyte growth factors and has a hemopoietic stem cell augmenting activity, which is characterized in that the transformant is cultured under the conditions in which said protein can be expressed in a culture medium and the recombinant human hepatocyte growth factor protein, which is one type of hepatocyte growth factor and has a hemopoietic stem cell augmenting activity, is prepared from the culture. In particular, the present invention relates to a recombinant which is derived from human normal fibroblasts and considered preferably from fibroblasts of the highest normality, and a process for the preparation of the same and use of the same.

An agent which contains at least one type of hepatocyte growth factor disclosed in the present invention as an active component is effective for use as a therapeutic agent for bone marrow suppression or as a therapeutic agent for bone marrow malfunctions.

An agent which contains at least one type of hepatocyte growth factor disclosed in the present invention as an active component is effective for in vitro growth of peripheral blood stem cells and bone marrow stem cells, and thus the present invention also provides a process for in vitro proliferation or the cultivation of stem cells using said agent.

BRIEF DESCRIPTION OF THE DRAWINGS

Figure 2F:
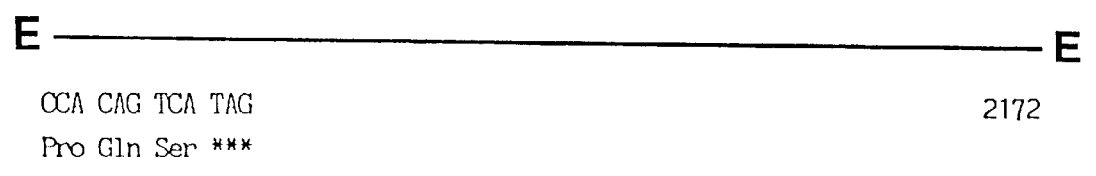

FIGS. 2A through 2E, when joined by match lines A-A through E-E, as shown in FIG. 2F, nucleotide sequence and an amino acid sequence of HGF cDNA derived from human normal fibroblasts.

BEST MODE FOR CARRYING OUT THE INVENTION

Figure 1:
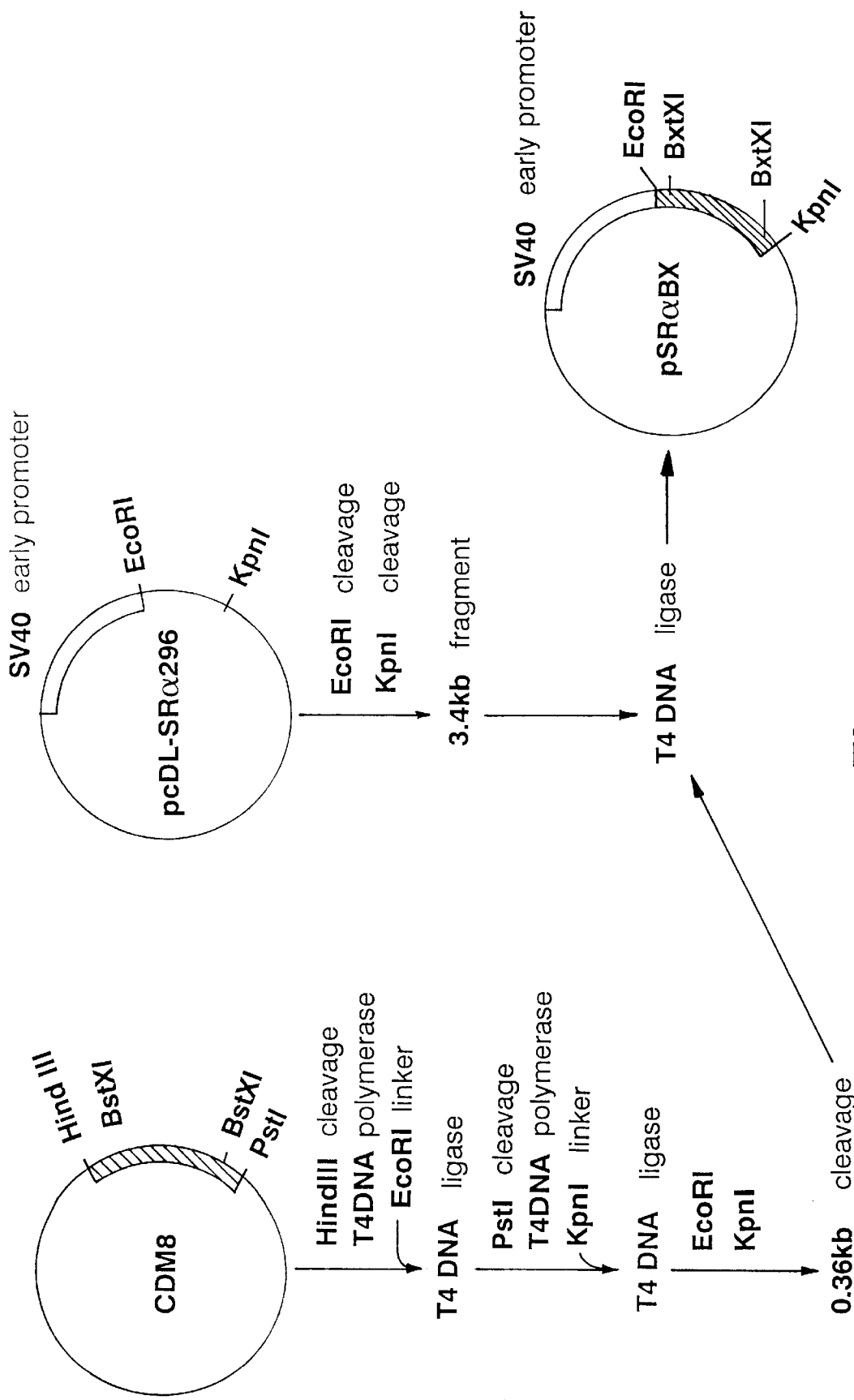
FIG. 1 illustrates a construction of an expression vector pSRalphaBX.

The present inventors focused their attentions on the fact that proliferation of cells of immature myeloblast cell line NFS 60 (Kevin L. Holmes et al., Proc. Natl. Acad. Sci. U.S.A., 82, 6687–6691, 1985) is dependent on interleukin 3 (IL-3) and that among the hemopoietic factors so far known, IL-3 is one of the cytokinins acting on undifferentiated hemopoietic stem cells and intensively searched for hemopoietic stem cell augmenting factors other than IL-3, using the augmenting activity on NFS60. As a result, the present inventors discovered a factor, which has hemopoietic stem cell augmenting activity, in the fibroblasts which are known to produce hemopoietic factors such as interleukin 1 (IL-1), interleukin 6 (IL-6), interleukin 7 (IL-7), interleukin 8 (IL-8), interleukin 11 (IL-11) and the c-kit ligand and found that the factor is a novel factor which is a type of hepatocyte growth factor. Subsequently, the present inventors also found that this growth factor supports the growth of hemopoietic stem cells in an evaluation system using human bone marrow cells and murine bone marrow cells.

This novel factor is a novel physiologically active protein which has an activity to support the growth of pluripotent hemopoietic stem cells and has a molecular weight of about 60,000 and an N-terminal amino acid sequence of SEQ ID NO: 1 shown in Sequence Listing.

Furthermore, this novel factor has an amino acid composition shown in Table 1. Since the N-terminal amino acid sequence and the amino acid composition of the physiologically active protein of this novel factor are different from those of known proteins, this belongs to a novel hemapoietic factor.

The novel factor of the present invention can be obtained in a purified form as a physiologically active protein using a culture fluid obtained by culturing human normal fibroblasts as the starting material and using a combination of various types of chromatography.

Details of physico-chemical properties and biological properties of the physiologically active protein of the present invention thus obtained are as follows:

(1) Molecular weight:
  60,000 (by SDS-polyacrylamide gel electrophoresis; Laemmli U. K., Nature, 227, 680–685, 1970)
(2) N-terminal amino acid sequence (16 residues).
  Shown in SEQ ID NO: 1 in Sequence Listing.
(3) Amino acid composition
  Shown in Table 1.
(4) Biological activities
  A. Exhibits an augmenting activity on pluripotent myeloblasts derived from mice (NFS60).
  B. Exhibits an augmenting activity in combination with IL-3 or with IL-3 and interleukin-7 (IL-7) on bone marrow cells of 5-fluorouracil (5-FU)-treated mice.
  C. Exhibits an augmenting activity on hemopoietic stem cells derived from human normal bone marrow.

On the other hand, since this factor having the hemopoietic stem cell augmenting activity is a type of hepatocyte growth factor, the present inventors studied a growth factor which was reported as one type of hepatocyte growth factor and a typical hepatocyte growth factor (Nakamura, T. et al., Biochem. Biophys. Res. Commun., 122, 1450–1459, 1984) and considered this factor to have an proliferating activity on NFS60 strain. Furthermore, they also considered this augmenting factor to support the growth of hemopoietic stem cells in an evaluation system using human and murine bone marrow cells or to have the hemopoietic stem cell augmenting activity.

Further, some of the hepatocyte growth factors are reported to have physiological activities other than the augmenting activity on hepatic parenchyma cells, such as the mitogenic activity on epithelial cells (Gherardi, E. et al., Nature, 346, 228, 1990) and a cytotoxic activity on tumor cells (Higashio, K. et al., Biochem. Biophys. Res. Commun., 170, 397–404, 1990); however, an action on bone marrow hemopoietic stem cells was not known to date.

Furthermore, since a typical hepatocyte growth factor derived from the liver, one of the hepatocyte growth factors, was genetically cloned and the whole nucleotide sequence was determined (Nakamura et al., Nature, 342, 440–443, 1989), that may used as a hemopoietic stem cell augmenting agent in the present invention. Furthermore, the factor, a type of hepatocyte growth factor and used in the present invention as a hemopoietic stem cell augmenting agent, can also be produced by culturing cells such as human normal fibroblasts. Furthermore, the factor can be produced by taking out a gene from human normal fibroblasts or the like, applying genetic recombination technique to the gene thus obtained and culturing the resultant transformants.

Thus, according to the present invention, the novel factor can be obtained also using genetic recombination technique. This novel factor is characterized in that it has the amino acid sequence of SEQ ID NO: 2 in Sequence Listing. This novel factor can be obtained using a cloned cDNA as specifically explained hereinbelow.

The above-mentioned factor can be obtained in a purified form, for example, from a culture fluid obtained by culturing human normal fibroblasts as the starting material by means of using a combination of various kinds of chromatography.

Cells such as human normal fibroblasts can be grown or cultured using various kinds of conventional cell culture media. Examples of such media are those in which substances such as a carbon source, a nitrogen source, vitamins, amino acids and nucleotides are contained and substances selected from the group consisting of meat broth, peptone, casamino acid, yeast extract, fish meal extract, potatoes, malt Juice, cow's milk, blood, serum, hormones, antibiotics and cell growth factors are added if desired; media which are widely used in general and are commercially available can be used as they are or with appropriate modifications.

Examples of these media include RPMI-1640 medium, MEM medium, Dulbecco-Eagle medium, DMEM medium, McCoy 5A medium, Iscove's modified Dulbecco's medium and Ham F12 medium.

In the proliferation and cultivation of cells such as human normal fibroblasts as mentioned above, optimal conditions for the growth of said human normal fibroblasts, such as pH, temperature, aeration, stirring and frequency of medium exchange, can be appropriately determined, for example, by experiments.

In the cultivation of human normal fibroblasts, cell adhesion factors such as collagen, fibronectin, gelatin, poly-L-lysine and poly-D-lysine can be added or microcarrier beads made of dextran, polyacrylamide, polystyrene, gelatin, glass or the like can be used, if appropriate.

If desired, the human normal fibroblasts obtained by the above-mentioned cell proliferation or cultivation are subjected to induction, for example, by a treatment with conventional inducing agents such as poly I/C to induce the production of the novel protein which is a type of hepatocyte growth factor and has a hemopoietic stem cell augmenting activity; the protein of the present invention thus obtained is isolated by a conventional procedure.

Examples of isolation procedures include a method by ultrasonic destruction, mechanical destruction or freezing and thawing, a method by osmotic shock or the like and an isolation method in which a culture supernatant is precipitated, for example, using a protein precipitant.

In addition to the above-mentioned separation methods, the targeted protein can be purified by various kinds of isolation and purification methods which are widely used in general, utilizing physical properties and chemical properties of the protein.

Examples of these isolation and purification methods include solubilization by homogenization or sonication, extractions with buffer solutions containing various kinds of salts, solubilization or precipitation with acids or alkalis, or else extraction or precipitation with organic solvents, salting out by precipitation with protein precipitants such as ammonium sulfate, ultrafiltrations by dialysis or ultra-filtration using a membrane filter, adsorption chromatography, gel filtration chromatography or the like, ion exchange chromatography, reversed-phase chromatography, affinity chromatography, counter-current distribution chromatography, high-performance liquid chromatography, isoelectric point or gel electrophoresis; these methods are used alone or in combination if appropriate.

If the protein is derived from human normal fibroblasts, affinity chromatography using a carrier bound with a blue pigment (a blue gel carrier), a carrier bound with zinc via chelate bonds (a zinc chelate gel carrier), a carrier bound with heparin (a heparin gel carrier), a carrier bound with antibodies or the like can be advantageously used. In particular, the zinc chelate gel carrier (media), the blue gel carrier (media) and the heparin gel carrier (media) are preferably used. A method in which the zinc chelate gel carrier and the heparin gel carrier are used in combination is more preferably used; the order of the use of the carriers is not particularly restricted but the use of the zinc chelate gel carrier after the heparin gel carrier is particularly preferable.

An example of the zinc chelate gel carrier used in the present invention is a carrier in which exchangeable groups having chelating capacity, such as a bis-carboxymethylimino group [$N(CH_2COOH)_2$], are bound to agarose, cellulose, polyacrylamide gel or the like is treated in a solution of zinc salt such as zinc chloride. Preferably, a carrier in which zinc is bound via chelate bonds to an insoluble polysaccharide gel carrier, such as "Chelating Sepharose" (a product of Pharmacia) is used.

Purification of hepatocyte growth factors using the zinc chelate gel carrier is carried out as follows. Namely, first, a solution containing the hepatocyte growth factors is made to come into contact with and adsorbed onto the zinc chelate gel carrier. The adsorption can be done either by a batch method or a column method but the column method gives higher adsorption efficiency.

The elution can be carried out using an acidic buffer solution such as phosphoric acid, acetic acid and citric acid and preferably at pH 5 or below. However, in high ionic strength, elution at higher pHs is possible. Furthermore, a gradient elution in which a concentration of imidazole, histamine, glycine or ammonium chloride is gradually increased gives good results. It is also possible to use a method in which metal ions are depleted from gels using a chelating agent such as EGTA or EDTA.

The ionic strength can be increased by increasing the concentration of acids such as phosphoric acid, acetic acid and citric acid in a buffer solution or by adding neutral salts such as sodium chloride and potassium chloride (0.2 to 1.0 M).

The composition and volume of the eluent are not particularly restricted and the optimal conditions for elution are appropriately determined depending on co-existing proteins or contaminants, the amount of hepatocyte growth factors, a column size or the like.

The heparin gel carrier used in the present invention can be any insoluble carrier formed from a synthetic polymer, a polysaccharide in which cellulose, agarose or the like is the starting material and forms the backbone molecule, or the like to which heparin is bound. Examples of the heparin gel carrier include "Heparin-Sepharose CL-6B (a product of Pharmacia), "Heparin Toyopearl" (a product of Toso) and "Heparin Cellulofine (a product of Chisso).

In the case where a solution containing hepatocyte growth factors is allowed to come into contact with the heparin gel carrier, it is desirable to control the pH between 5 and 10. In particular, a pH between 5.5 to 8.0 and ionic strength of 0.3 or less are preferable to sufficiently ensure an affinity to heparin. Thus, the hepatocyte growth factors adsorbed onto the heparin gel carrier can be recovered by increasing the ionic strength. For example, the recovery can be achieved by using a buffer solution such as sodium phosphate buffer with an addition of inorganic salts such as sodium chloride and ammonium sulfate. The method for the recovery can be a method in which the salt concentration is increased either in a gradient system or a step-wise system. Specifically, the ionic strength to be used is in a range of 0.3 to 3, preferably 0.5 to 2.

The natural-type protein which is a type of hepatocyte growth factor and has a hemopoietic stem cell augmenting activity, which is purified and isolated as described above, can be hydrolyzed using an acid such as hydrochloric acid or proteinases such as pepsin, chymotrypsin and carboxy peptidase; peptide fragments thus obtained are subjected to chromatography such as ion-exchange chromatography to determine their amino acid compositions as well as amino acid sequences.

A process for the analysis of the amino acid composition of the natural-type protein of the present invention, which is a type of hepatocyte growth factor and has the hemopoietic stem cell augmenting activity, will be explained in detail. First, said protein which is a type of hepatocyte growth factor and has the hemopoietic stem cell augmenting activity is hydrolyzed with hydrochloric acid and then the resulting amino acids are converted into corresponding phenylthiocalbamyl derivatives by reaction with phenylisothiocyanate (PITC); the derivatives are then quantitatively analyzed by reversed-phase high performance liquid chromatography (a PITC method).

The amino acid sequence thus obtained can be utilized when the natural-type protein which is a type of hepatocyte growth factor and has the hemopoietic stem cell augmenting activity is produced using genetic recombination techniques.

Next, a process using typical genetic recombination technique for the preparation of the factor, which is a type of hepatocyte growth factor and is used as a hemopoietic stem cell augmenting agent according to the present invention, will be given below.

Methods for obtaining RNA from human normal fibroblasts include the application of conventional processes such as isolation of polysome, sucrose density gradient centrifugation and electrophoresis. An appropriate method for extracting RNA from the above-mentioned human normal fibroblasts can be selected from various methods including the guanidine thiocyanate-cesium chloride method in which CsCl density gradient centrifugation is carried out after the treatment with guanidine thiocyanate (Chirgwin et al., Biochemistry, 18, 5294, 1979), a method in which a vanadium complex is treated with a surface action agent in the presence of a ribonuclease inhibitor, and then further treated with phenol (Berger et al., Biochemistry, 18, 5143, 1979), a guanidine thiocyanate-hot phenol method, a guanidine thiocyanate-guanidine hydrochloride method, a guanidine thiocyanate-phenol chloroform method and a method in which after the treatment with guanidine thiocyanate, RNA is precipitated by treatment with lithium chloride. mRNA is isolated from human normal fibroblasts by a conventional method such as the lithium chloride/urea method, guanidine isothiocyanate method and oligo-dT cellulose column method. cDNA is synthesized from mRNA thus obtained using a conventional method such as a method of Gubler et al. (Geen, 25, 236–269, 1983) and a method of H. Okayama et al. (Mol. Cell. Biol., 2, 161, 1982; ibid., 3, 280, 1983). In order to synthesize cDNA from the obtained mRNA, a reverse transcriptase, for example, of avian myeloblastosis virus is principally used, but a method using DNA polymerase can also be used in combination with the partial use of a primer; however, it is convenient to use a commercially available kit for the synthesis or cloning.

The cDNA thus prepared is incorporated in an expression vector, plasmid or baccteriophage and using this recombinant DNA, a cDNA library is constructed with the use of *Escherichia coli*, according to conventional methods such as the method of Seed (Nature, 329, 840–842, 1987).

To incorporate the above-mentioned cDNA into a vector, a conventional method is applied, using the cohesive ends created using the same restriction enzymes, or synthesized linker site or adapter site are added if necessary, or a homo-polymer is added.

These procedures can be carried out, according to conventional methods (Molecular Cloning, Cold Spring Harbor Laboratory, New York, 1982). The vectors and plasmids into which the cDNA is incorporated are, for example, CDM8, pcDL-SRalpha296, pBR322, pUC18, pUC19 and pUB110 but are not limited to these examples; any vectors and plasmids which are conventionally used for the incorporation of cDNA may be used. Vectors and plasmids which are used to make a cDNA library using *E. coli* are preferable. In the case where a vector for the incorporation of cDNA is a phage, for example, lambda-gt10 and lambda-gt11 are used but are not limited to these examples; any phages which are conventionally used for the incorporation of cDNA may be used.

In order to introduce a recombinant vector thus obtained into a host, various kinds of conventional methods may be used.

In the case where the vector is a plasmid, an example of a method includes the one in which the vector is introduced into competent cells prepared according to a method of Hanahan et al. (J. Mol. Biol., 166, 557, 1983) in the presence of $CaCl_2$ or RbCl. In the case where the vector is a phage, an example of a method is the one in which recombinant phage vector is infected into host cells in an appropriate growth phase using an in vitro packaging method or the like.

Examples of the host cells which maintain the CDNA library thus obtained include specifically *E. coli* MC1061/P3, NM514, NM522, JM101 and C600; however, they are not limited to these examples and any conventional host cells which maintain the cDNA library may be used.

Next, based on the nucleotide sequence of the N-terminal and C terminal of the human hepatocyte growth factor, which is a type of hepatocyte growth factor (Nakamura et al., Nature, 342, 440–443, 1989), an oligonucleotide for use as a probe was synthesized; using this probe in which the oligonucleotide is labeled with $^{32}P$, the targeted cDNA can be obtained by a method such as a colony hybridization method, plaque hybridization method, hybridization-translation assay method and plus-minus method.

More specifically, the DNA in a plaque of the recombinants is immobilized on a filter such as a nylon membrane and then reacted with the labeled probe to select the recombinants having the DNA sequence which binds selectively with this probe.

The above-mentioned probe to be used herein refers to the nucleotide sequence which is complementary to the targeted DNA sequence; the probe can be either DNA or RNA, either chemically synthesized or natural, or else those obtained by the recombinant DNA method; the use of a DNA sequence which is chemically synthesized by means of a known method is general and preferable.

Examples of methods of synthesizing oligonucleotides used herein include conventional methods used for chemical synthesis of nucleic acids, such as the phosphotriester method (Tetrahedron, 34, 3143, 1978; Adv. Carbohydr. Chem. Biochem., 36, 135, 1979; Nucleic Acids Res., 10, 2597, 6553, 1982) and phosphoamidite method (Nature, 310, 105, 1984) and combinations of these methods.

Next, another method can be used, in which based on the one N-terminal and C-terminal sequence of the above-mentioned human hepatocyte growth factor, which is a type of hepatocyte growth factor (Nakamura et al., Nature, 342, 440–443, 1989), two kinds of primers are synthesized by a DNA synthesizer; in the presence of a DNA polymerase such as Taq DNA polymerase together with each of the primers and cDNA, denaturation of the DNA and then annealing of the primers are allowed to proceed and the elongation reaction of the primers is carried out, for example, using a DNA thermal cycler (a product of Perkin-Elmer Cetus). The resultant product is subjected to electrophoresis and then the targeted cDNA of human hepatocyte growth factor, which is a type of hepatocyte growth factor (HGF) can be prepared according to the conventional method (Molecular Cloning, Cold Spring Harbor Laboratory, New York, 1982).

Furthermore, another method can also be used, in which primers are synthesized using a DNA synthesizer based on the 16 amino acid sequence in one N-terminal nucleotide sequence of the human hepatocyte growth factor, which is a type of hepatocyte growth factor and is obtained by culturing cells such as human fibroblasts, in the presence of a DNA polymerase such as Taq DNA polymerase together with each of the primers and then the denaturation of DNA followed by the annealing of the primers are allowed to proceed and the elongation reaction of the primers is carried out, for example, using a DNA thermal cycler (a product of Perkin-Elmer Cetus). The resultant product is subjected to electrophoresis and then the targeted cDNA of human hepatocyte growth factor, which is a type of hepatocyte growth factor (HGF) can be prepared according to the conventional method. Further, it is observed that when the genes, primers as well as probes of different sources are used, various cDNAs for the human hepatocyte growth factor, which is a type of hepatocyte growth factor, having different nucleotide sequences are accordingly obtained.

The recombinant DNA thus obtained is treated with restriction enzymes or the like and the nucleotide sequence of the cDNA is determined according to the conventional method. The nucleotide sequence of the cDNA is obtained by a method such as the Maxam Gilbert method, the dideoxy method of Sanger such as the dideoxy nucleotide chain termination method (Sanger, Science, 214, 1205, 1981; Methods in Enzymology, 65, 560–580, 1980; Messing, J. et al., Nucleic Acids Res., 9, 309, 1981). Furthermore, the cDNA is synthesized by a primer extension method using the above-mentioned isolated mRNA and a part of the sequenced cDNA and then the recombinant DNA can be obtained as described above.

These methods can be used in appropriate combinations.

Since cleavage, deletion, addition and binding of DNA chains and furthermore substitutions of nucleotides in the DNA chains according to genetic recombination techniques, can be carried out by conventional procedures, the DNA of the present invention relates not only to the DNA having the nucleotide sequence of SEQ ID NO: 2 in Sequence Listing but also to the above-mentioned altered or modified forms to the extent within the scope of the present invention.

Typical methods for the above-mentioned alteration include a method known as oligonucleotide directed mutagenesis, a method of M. Smith and S. Gillam (Genetic Engineering (J. K. Setlow and A. Hollaender eds, Vol. 3, p.1, 1981) and the methods described in Methods in Enzymology, Vol. 153–155, 1987, Academic Press, CA) and the methods in the references cited in the same.

A particularly preferred method for the alteration and modification of the gene having the nucleotide sequence shown in SEQ ID NO: 2 in Sequence Listing is a method to increase the stability of the targeted protein and to increase biological activity.

Furthermore, there is an altered and modified method in which among the activities of the peptide having the amino acid sequence shown in SEQ ID NO: 2 in Sequence Listing, the activity of proliferation of undifferentiated pluripotent hemopoietic stem cell can be increased.

The cloned cDNA which contains the nucleotide sequence coding for all or part of the amino acid sequence of the protein which is a type of hepatocyte growth factor and has the hemopoietic stem cell augmenting activity, or a substance equivalent in terms of effectiveness is deemed to be a recombinant expression vector in which said coding nucleotide sequence is so incorporated as to be expressed.

In particular, the cDNA which contains the nucleotide sequence coding for all or part of the sequence of the protein or a substance equivalent in terms of effectiveness having the amino acid sequence of SEQ ID NO: 2 in Sequence Listing can be recombined in a suitable expression vector and then the recombinant vector is introduced into an appropriate host cell to form transformants; the transformants thus prepared are cultured and the protein having the targeted hemopoietic stem cell augmenting activity can be obtained by appropriately inducing the expression; the cDNA being thus useful.

In the production of the targeted protein in the host cells using the cDNA which contains the nucleotide sequence coding for all or part of the amino acid sequence of the protein of the present invention, which is a type of hepatocyte growth factor and has the hemopoietic stem cell augmenting activity, or a substance equivalent in terms of effectiveness, the protein can be produced as a mature protein, namely in a form from which signal peptides are removed, or with the above-mentioned signal peptides as they are, or else signal peptides compatible in appropriate host cells or the like are added to and the protein can be produced by secretion from the host cells or the like.

Furthermore, the protein of the present invention, which is a type of hepatocyte growth factor and has the hemopoietic stem cell augmenting activity, or a substance equivalent in terms of effectiveness can be produced as a fused protein or peptide with other recombinant protein or peptide and then the targeted protein is isolated or obtained without isolation by digestion or treatment with enzymes or chemicals from the fused proteins.

In order to effectively express the protein of the present invention, which is a type of hepatocyte growth factor and has the hemopoietic stem cell augmenting activity, or a substance equivalent in terms of effectiveness, the cDNA containing its coding nucleotide sequence can be located at the down stream region which is under the control of a promoter, a ribosome binding site (for example, the SD sequence), a translation initiation site or codon, and then a termination site or codon and a terminator can be located. Namely, in this case, a initiation codon and a stop codon are necessary in the DNA sequence of the gene for its use and are added if necessary using known methods.

As the expression vector to be used herein is not specifically restricted and any vectors which can be autonomously replicable are usable; vectors which contain a replication origin, a selection marker, a promoter, an RNA splicing site and a polyadenylation signal or the like are preferably used.

Examples of the selective marker of the recombinant expression vector include various antibiotic resistant genes, such as ampicilin resistant gene, tetracycline resistant gene and neomycin resistant gene.

Furthermore, examples of the vectors include those derived from various bacteria, those derived from bacteriophages, those derived from animal viruses including insect viruses and mammalian cell viruses, namely, various virus vectors, various plasmid vectors, cosmid vectors, shuttle vectors or the like.

Furthermore, examples of these vectors include *E. coli*, particularly EK-type plasmid vector, lambda-gt-type phage vectors, vectors derived from *Pseudomonas aeruginosa*, vectors derived from *Bacillus subtilis*, vectors derived from yeast, vectors derived from SV40, vectors derived from BPV and vectors derived from retrovirus. Specifically, the examples include pBR322, pUC18, pUB110, pRB15, lambda-gt10, lambda-gt11, SV40 and BPV.

The promoters to be used in the above-mentioned vectors have no particular restriction as long as they can promote expression in the host. Examples of promoters for expression include a tryptophan (trp) promoter, lactose (lac) promoter, a tryptophan/lactose (tac) promoter, a T7 promoter and a lambda-PL promoter which are well known to those skilled in various fields.

Examples of the promoters which are used in vectors for yeast and are typical regulation sequences include promoters relating to the synthesis of enzymes in glycolysis, such as a promoter relating to glycerate-3-phosphokinase, a promoter relating to glyceraldehyde-3-phosphate dehydrogenase, promoters relating to hexokinase, pyruvate decarboxylase, fructose phosphokinase, glucose-6-phosphate isomerase, 3-phosphate isomerase, phosphoglucose isomerase, glucose kinase or the like, or else promoters relating to alcohol dehydrogenase, chytochrome C, acid phosphatase or the like.

Examples of promoters which are be compatible in mammalian cells include an SV40 early-stage gene or late-stage gene promoter, promoters derived from cytomegalovirus, polyoma virus, adeno virus, bovine papillomavirus or avian sarcoma virus, promoters relating to moloney mouse sarcoma virus LTR, rous sarcoma virus LTR, mouse mammary cancer virus LTR and methallothionein, promoters relating to immunoglobulins, promoters relating to heat shock, promoters relating to dehydrofolic acid, promoters relating to actin and promoters relating to elongation factors.

For insect cells, a promoter relating to polyhydrin derived from nuclear polyhederosis disease virus can be used.

These gene regulating sequences are incorporated into an appropriate vector in combination or in chemically modified form if appropriate and used to construct a vector for the expression of the cDNA which contains the nucleotide sequence coding for all or part of the amino acid sequence of the protein of the present invention, which is a type of hepatocyte growth factor and has the hemopoietic stem cell augmenting activity, or a substance equivalent in terms of effectiveness.

For example, the sequence can contain a translation initiation codon ATG and a termination codon TAA, TGA or TAG as a gene regulating sequence of the cDNA of the present invention; they can be arranged in multiple numbers or in combination with other codons.

In the vectors for the expression of the cDNA of the present invention, a multiple number of the cDNA of the present invention can additionally be incorporated to be expressed.

The vector for the expression of the cDNA which contains the nucleotide sequence coding for all or part of the amino acid sequence of the protein of the present invention, which is a type of hepatocyte growth factor and has the hemopoietic stem cell augmenting activity, or a substance equivalent in terms of effectiveness can be used to obtain a large quantity of cells called transformant which are capable of producing all or part of the amino acid sequence of the protein, which is a type of hepatocyte growth factor and has the hemopoietic stem cell augmenting activity, or a substance equivalent in terms of effectiveness, by a process in which the cDNA is introduced into an appropriate host according to a conventional method which is specifically known for the corresponding host cells and then transform the host cells, and the host cells thus transformed were multiplied by a culture method or the like.

The hosts, particularly cells, herein used can be any cells of *E. coli* or gram-negative bacteria other than *E. coli*, such as Pseudomonas, gram-positive bacteria such as *Bacillus subtilis* and actinomyces or eukaryotic cells such as yeast, mammalian cells, insect cells, plant cells; however, *E. coli* and mammalian cells such as COS cells and CHO cells are preferably used.

Any methods which are conventionally used in the field of genetic recombination technology can be used as a process for the induction of the gene expression vectors of the present invention into the above-mentioned host cells;

examples of methods include a method in which competent cells and the above-mentioned vectors are mixed, a method in which host cells are converted to protoplasts after which the above-mentioned vectors bound to a carrier are introduced into the protoplasts, or a calcium phosphate co-precipitation method, a DEAE dextran method, an electroporation method, an in-vitro packaging method, a virus vector method and a microinjection method.

The transformants thus obtained can be grown under the conditions in which expression of foreign genes therein is suppressed and then the expression of the targeted gene is induced.

The growth or the cultivation of the transformants can be carried out using various kinds of conventional media for cell culture in the same manner as in the case of the above-mentioned human normal fibroblasts. Other growth conditions, culture systems as well as processes for the isolation and purification of the protein are the same as in the case of human normal fibroblasts. The hemopoietic stem cell augmenting agent of the present invention has an activity to augment undifferentiated pluripotent hemopoietic stem cells and is useful as an active hemopoietic stem cell augmenting agents for the treatment of bone marrow suppression (for example after the use of anti-cancer agents or bone marrow transplantation), as an active hemopoietic stem cell augmenting agent for the treatment of bone marrow malfunctions (such as hypoplastic anemia and osteomyelodysplasia syndrome) or as an active hemopoietic stem cell augmenting agent for the in vitro proliferation of peripheral stem cells and bone marrow stem cells.

Furthermore, since the hemopoietic stem cell augmenting agent eventually promote the growth of not only a variety of blood cells but also progeny of hemopoietic stem cells, osteoclasts, it is applicable as a therapeutic agent for osteoporosis or the like.

In the present invention, particularly, the recombinant human normal fibroblast protein which is a type of hepatocyte growth factor and has the amino acid sequence of SEQ ID NO: 2 in Sequence Listing, or a substance equivalent in terms of effectiveness, is preferably used as a hemopoietic stem cell augmenting agent, exhibits an augmenting activity on pluripotent hemopoietic stem cells, is an active hemopoietic stem cell augmenting agent to restore bone marrow growth (for example after the use of anti-cancer agents or bone marrow transplantation), is an active hemopoietic stem cell augmenting agent for the treatment of bone marrow malfunctions (such as hypoplastic anemia and osteomyelodysplasia syndrome) or is an active hemopoietic stem cell augmenting agent for the in vitro proliferation of peripheral blood stem cells and bone marrow stem cells. The protein is derived from human normal fibroblasts and accordingly is a relatively normal-type, which is considered to be preferable.

Furthermore, a corresponding natural-type protein obtained from human normal fibroblasts is considered to be preferable as a hemopoietic stem cell augmenting agent and is useful in the above-mentioned utilization.

In the cases where the hemopoietic stem cell augmenting agent of the present invention is used for the above-mentioned uses according to the present invention, it can be administered orally or parenterally as it is or as a pharmaceutical composition mixed with a pharmaceutically acceptable vehicle, an excipient or the like, which is known per se.

In order to maintain an active component in the hemopoietic stem cell augmenting agent of the present invention, amino acids such as arginine, lysine, glycine, leucine, phenylalanine and aspartic acid, saccharides such as glucose, sucrose, mannitol and mannit, polysaccharides or protein hydrolysates such as sugar alcohol, gelatin, collagen, dextran, pullulan, heparin, chondroitin sulfate and cellulose, inorganic acids such as hydrochloric acid or organic acids such as acetic acid, inorganic bases such as sodium hydroxide or inorganic bases such as amines or the like can be added when appropriate.

Dosage forms of the preparations for oral administration are specifically tablets, pills, capsules, syrups, emulsions, suspensions or the like. The preparations in such forms can be manufactured by the methods known per se and contain vehicles or excipients which are conventionally in the pharmaceutical field. Examples of vehicles and excipients for tablets include lactose, starch, sucrose and magnesium stearate.

Dosage forms of preparations for parenteral administration are, for example, ointment, injectable preparations, wet compressing agents, endermic liniments, agents, inhalants, suppositories, percutaneous vapors or the like. The injectable preparations can be prepared according to means known per se such that the hepatocyte growth factor of the present invention is dissolved, suspended or emulsified in a sterilized aqueous or oily solution which is conventionally used for injectable solutions. Examples of the aqueous solutions for injectable solutions include physiological saline and glucose solutions and examples of the oily solutions include sesame oil and soybean oil; in each case solubilizers may be used in combination. Suppositories used for rectal administration are prepared by means known per se such that the hemopoietic stem cell augmenting agent of the present invention is mixed with a conventional base for suppositories and the mixture is formulated.

The effective quantity and number of doses of the hemopoietic stem cell augmenting agent of the present invention depends on such factors as mode of administration, age and body weight of patient and property and severity of the particular disease to which the therapy is applied; however, in general, the daily dose for an adult is between 0.01 and 100 mg, preferably between 0.1 and 10 mg in one dose or in divided doses.

The novel protein of the present invention, which is a type of hepatocyte growth factor and has a hemopoietic stem cell augmenting activity, or a substance equivalen in terms of effectiveness can produce antibodies in such a way that the protein or its equivalent alone or in a form conjugated with a vehicle such as bovine serum albumin, egg serum albumin, thioglobulin or hemocyanin (KLH) by means of, for example, carbodiimide, glutaraldehyde, mixed acid anhydrates, homo-difunctional or hetero-difunctional reagents (e.g. maleidobenzyl-N-hydroxysuccinimide ester (MBS) or the like is injected to an animal for immunization. Furthermore, spleen cells obtained from the animal such as a mouse thus immunized and myeloma cells are fused according to the conventional method and thus hybridoma cells to produce monoclonal antibodies can be obtained.

The antibodies thus obtained can be made into a reagent for measurement by binding onto a solid phase, or by binding with, for example, enzymes, co-enzymes, fluorescent substances, coloring agents such as dye, radio-active labels or paramagnetic metals. Examples of standard methods for immunoassay are an enzyme-linked immunoassay (ELISA), a radio immunoassay (RIA) and a sandwich immunoassay.

These assay are carried out according to D. Catty, "Antibodies—Vol. I & Vol. II, A practical approach", IRL Press.

EXAMPLES

The invention is further illustrated by the following examples but the invention is not limited to these examples.

Example 1

Preparation of human hepatocyte growth factor derived from normal fibroblasts:

Using a 30-l culture bath, cells of human normal fibroblast DIP2 (Kobayashi, S. et al., In The clinical potential of interferons, ed. Kono, R. and Vilcek, J., University of Tokyo Press, Tokyo, 1982) were cultured on 10% FBS-MEM medium-0.3% beads (Cytodex-1, Pharmacia) at 37° C. for 5 days with stirring. When growth reached the confluent state, the medium was changed to a fresh MEM medium and protein production was induced by the addition of poly I/C (10 micrograms/ml). The incubation was continued at 37° C. for another 4 days and then 20 liters of culture supernatant were recovered.

The culture supernatant was adsorbed on a "Blue Sepharose Column" (1 liter gel carrier; Pharmacia) equilibrated with a 20 mM tris-HCl buffer solution (pH 8.0) and then the column was washed with the same buffer used for the equilibration. Subsequently, proteins were eluted using a 0–3 M linear NaCl concentration gradient.

Figure 9:
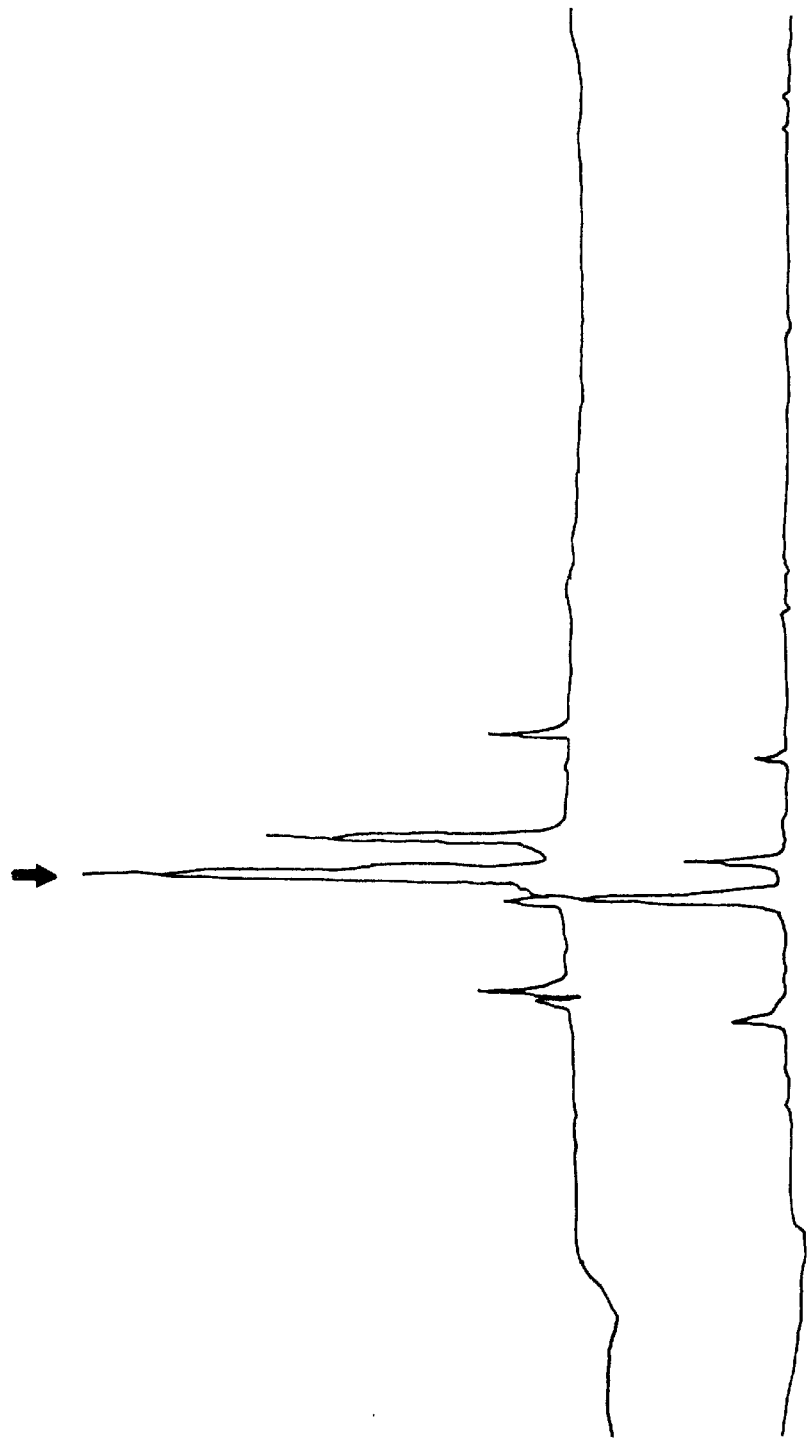
FIG. 9 is a chromatogram of reversed-phase high performance liquid chromatography as described in Example 1.

One liter of an active fraction thus obtained was desalted by gel filtration and then the desalted fraction was adsorbed on a heparin-Sepharose column (gel carrier 100 ml; Pharmacia) equilibrated with a 20 mM tris-HCl buffer solution (pH 8.0) and the column was washed with the same buffer used for the equlibration. Subsequently, proteins were eluted using a 0–3 M NaCl linear concentration gradient. 50 ml of an active fraction thus obtained was desalted by gel filtration and then purified by reversed-phase high performance liquid chromatography. Using a "Vydac 218TP510 Column" (1.0×25 cm; Separation Group), elution was carried out using a 0–50% acetonitrile linear concentration gradient in a 0.1% aqueous trifluoroacetic acid solution. Results are shown in FIG. 9.

A fraction of the active peak was subjected to SDS polyacrylamide electrophoresis under reducing conditions (Laemmli U. K., Nature, 227, 680–685, 1970); a single band at a molecular weight of about 60K was obtained.

Example 2

N-terminal amino acid sequence and amino acid composition:

The purified protein obtained in Example 1, which is a natural-type human hepatocyte growth factor derived from fibroblasts, (referred to as natural-type human HGF hereinafter) was placed in an amino acid sequencer (Applied Biosystems 477A Protein Sequenser); as a result, the sequence of 16 amino acids at the N-terminal was determined as shown in SEQ: ID NO: 1 in Sequence Listing. Judging from the homology in sequence of this N-terminal sequence with that disclosed by Nakamura et al. (Nature, 342, 440–443, 1989), this sequence was revealed to be the N-terminal of the beta chain.

25 microliters of conc. hydrochloric acid containing 0.4% thioglycolic acid was added at a concentration of 4 micrograms/25 microliters; after hydrolysis at 110° C. for 22 hours in a tube sealed in vacuum, the hydrochloric acid was dried under reduced pressure. The resultant product was dissolved in distilled water and subjected to amino acid analysis using an amino acid analyzer (Hitachi 835-type amino acid analyzer 9). Results are shown in Table 1.

TABLE 1

| Amino acid | Mol % | Amino acid | Mol % |
|---|---|---|---|
| Asp + Asn | 12.85 | Met | 2.00 |
| Thr | 5.76 | Ile | 5.27 |
| Ser | 6.31 | Leu | 5.87 |
| Glu + Gln | 9.67 | Tyr | 4.73 |
| Pro | 5.95 | Phe | 2.72 |
| Gly | 9.91 | Lys | 6.45 |
| Ala | 3.86 | His | 3.45 |
| ½ Cys | 3.31 | Trp | 1.21 |
| Val | 4.83 | Arg | 5.86 |

Example 3

Cloning of human hepatocyte growth factor CDNA derived from normal fibroblasts:

Since cDNA of human hepatocyte growth factor had been cloned and sequenced by Nakamura et al. (Nature, 342, 440–443, 1989), a primer was synthesized based on the sequence; after replicating cDNA by the polymerase chain reaction (PCR) method, the cDNA can be cloned in, for example, an expression vector.

(1) Isolation of human normal fibroblasts mRNA:

RNA was prepared from human normal fibroblasts MRC5 (RCB211, available at Riken Cell Bank, Japan), which was cultured in the same manner as in Example 1, according to a lithium chloride/urea method (Auffray et al, Eur. J. Biochem., 107, 303–314, 1980). RNA thus obtained was dissolved in a 10 mM tris-HCl buffer solution (pH 7.5) containing 1 mM EDTA (referred to as TE hereinafter) and after heating the solution at 70° C. for 5 minutes, an equal amount of TE containing 1 M LiCl was added to the solution. The resultant RNA solution was applied on an oligo-dT cellulose column which had been equilibrated with TE containing 0.5 M LICl and the column was washed with the same buffer solution. The column was further washed with TE containing 0.3 M LiCl and then adsorbed poly (A) RNA was eluted with 2 mM EDTA (pH 7.0) containing 0.01% SDS.

(2) Construction of cDNA library derived from human normal fibroblasts:

cDNA was prepared using 4 micrograms of poly (A) RNA obtained as described in (1) above, according to the method of Gubler et al. (Geen, 25, 236–269, 1983).

This cDNA was inserted in an expression vector CDM8 using T4 DNA ligase according to the method of Seed (Nature, 329, 840–842, 1987). Using this recombinant DNA, *E. coli* MC1061/P3 was transformed to obtain cDNA libraries. The titration revealed that this cDNA library consisted of 200 thousand transformants. Plasmid DNAs were isolated from these transformants according to the conventional method (Molecular Cloning, Cold Spring Harbor Laboratory, New York, 1982).

(3) Isolation of human hepatocyte growth factor cDNA derived from normal fibroblasts:

Appropriate sequences are selected from the amino acid sequence of the human hepatocyte growth factor: for example, a nucleotide sequence of the N-terminal or C-terminal is selected and two kinds of primers are synthesized base on the selected sequence by a DNA synthesizer; after amplifying cDNA by the polymerase chain reaction (PCR) method, the products are cloned in an expression vector or the like.

Two kinds of primers having the following sequences were synthesized by a DNA synthesizer based on the human hepatocyte growth factor sequences of the N-terminal and C-terminal of a human hepatocyte growth factor derived from the liver, known as a human hepatocyte growth factor (Nakamura et al., Nature, 342, 440–443, 1989).

5' ATGTGGGTGACCAAAC 3' (SEQ ID NO:4)

and

5' CTAThrTGACCys TGTTrp GGTThoACC 3' (SEQ ID NO:5)

20 pmol of each primer and 1 microgram of the plasmid DNA obtained in the above-mentioned (2) were placed in a micro-centrifuge tube and then various reagents were added to the tube to make a mixture of a total volume of 100 microliters containing 20 mM tris-HCl buffer (pH 8.3), 1.5 mM MgCl$_2$, 25 mM KCl, 100 micrograms/ml gelatin, and 50 microM each of dNTP, and 4 unit Taq DNA polymerase. The resulting mixture was subjected to reactions of 40 cycles using a DNA thermal cycler (Perkin-Elmer Cetus) in which the conditions for DNA denaturation were at 94° C. for 1 minute, the conditions for primer annealing were at 50° C. for 3 minutes and the conditions for primer extension were at 72° C. for 3 minutes. The reaction product was subjected to a 1% agarose-gel electrophoresis and a human hepatocyte growth factor cDNA derived from normal fibroblasts, having a size of about 2.2 kb, was prepared according to the conventional method (Molecular Cloning, Cold Spring Harbor Laboratory, New York, 1982).

Alternatively, the human hepatocyte growth factor derived from normal fibroblasts can be obtained by a colony hybridization method in which an oligomer is synthesized by a DNA synthesizer based on the amino acid sequence (having 16 amino acids) of the N-terminal of the human hepatocyte growth factor derived from human normal fibroblasts prepared as described in Example 1.

(4) Preparation of expression vector:

An expression vector CDM8 (Seed, Nature, 329, 840–842, 1987) was digested with restriction enzyme HindIII, and blunt ends were made with T4 DNA polymerase and an EcoRI linker was herein ligated using T4 DNA ligase. Then, the resultant fragment was digested with restriction enzyme PstI and blunt ends were made using T4 DNA polymerase. A KpnI linker was ligated using T4 DNA ligase and then the resultant fragment was digested with restriction enzymes EcoRI and KpnI. The resultant product was subjected to 1% agarose-gel electrophoresis and a DNA fragment of about 0.36 kb was prepared according to the conventional method. On the other hand, pcDL-SRalpha296 (Takebe et al., Mol. Cell. Biol., 8, 446–472, 1988) was digested with restriction enzymes EcoRI and KpnI and a DNA fragment of about 3.4 kb was subsequently purified by agarose-gel electrophoresis; the vector thus obtained was ligated with the DNA fragment of about 0.36 kb obtained as described above, using T4 DNA ligase. Using this product, E. coli was transformed by the conventional method and a plasmid DNA was obtained from the resultant transformant according to the conventional method (Molecular Cloning, Cold Spring Harbor Laboratory, New York, 1982) and then a targeted expression vector, pSRalphaBX was obtained.

FIG. 1 illustrates the construction of expression vector pSRalphaBX.

This plasmid DNA was digested with restriction enzyme BstXI and the reaction solution was subjected to 1% agarose-gel electrophoresis, thereby a DNA fragment of 3.4 kb both ends having a restriction enzyme BstXI cleavage site was isolated and purified.

(5) Cloning of human hepatocyte growth factor cDNA derived from normal fibroblasts into expression vector and determination of nucleotide sequece:

The 2.2 kb cDNA fragment of the human hepatocyte growth factor derived from normal fibroblasts which was obtained as described above in (3) was phosphorylated using T4 DNA kinase according to the conventional method (Molecular Cloning, Cold Spring Harbor Laboratory, New York, 1982) and then ligated with a BstXI linker (N408-18; Invitrogen) using T4 ligase. Subsequently, this reaction mixture was subjected to 1% agarose-gel electrophoresis, whereby a DNA fragment of 2.2 kb ligated with BstXI linker was isolated and purified. This DNA fragment was ligated using T4 ligase with the DNA fragment of 3.4 kb obtained in the above-mentioned (4), in which both ends were digested with restriction enzyme BstXI. Using this product E. coli was transformed and a plasmid DNA was prepared according to the conventional method from the transformant thus obtained. Subsequently, the plasmid carrying the CDNA fragment of human hepatocyte growth factor derived from normal fibroblasts was confirmed by digestng this plasmid DNA with restriction enzyme BamHI (said plasmid is referred to as pSRαFDF-1 or pSRalphaFDF-1 hereinafter) and then the nucleotide sequence of the cDNA of hepatocyte growth factor derived from normal fibroblasts was determined by the dideoxy method (Prober et al., Science, 238, 336–341, 1987) using the Genesis 2000 DNA analysis system (DuPont) (FIG. 2).

Figure 3:
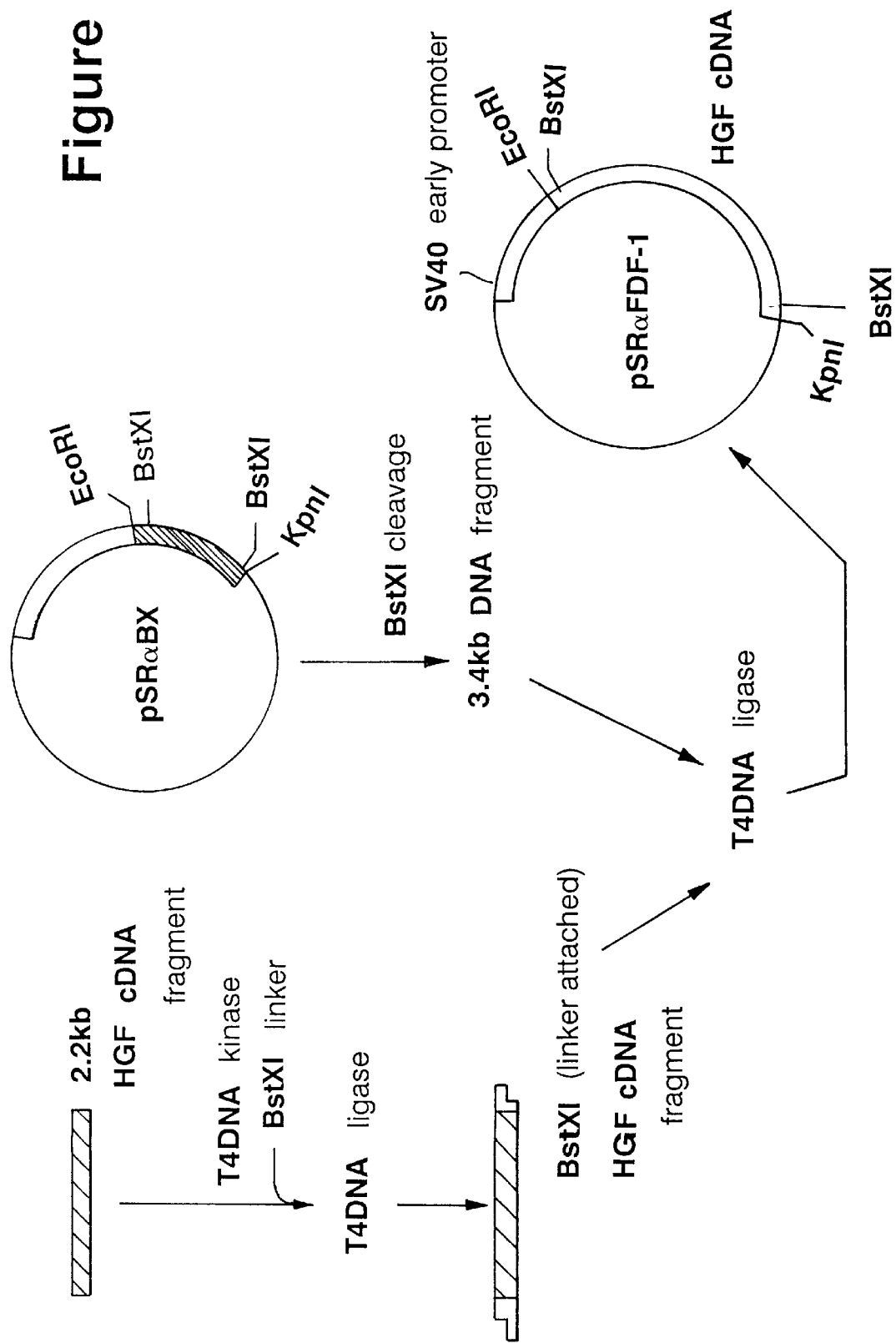
FIG. 3 illustrates a construction of a human HGF expression vector pSRalphaFDF-1 for the expression of mammalian cells.

FIG. 3 illustrates the construction of human HGF expression vector pSRαFDF-1 for expression in mammalian cells.

(6) Expression of human hepatocyte growth factor gene isolated from normal fibroblasts in monkey COS cells:

10 micrograms of pSRalphaFDF-1 obtained as described in (5) above was added to 4 ml of an RPMI164 medium containing 40 mM tris-HCl buffer (pH 7.5), 400 microgram/ml DEAE dextran (Pharmacia) and 100 microM chloroquine (Sigma). On the other hand, COS-1 cells (ATCC CRL-1650), which had been grown to confluent in an RPMI1640 medium (Gibco) supplemented with 10% fetal calf serum (Gibco), was washed once with PBS and then 4 ml of the above-mentioned DNA mixture was added to the cells, after which the incubation was carried out at 37° C. in an atmosphere of 5% $CO_2$. After 4 hours, cells were washed with PBS and then cultured in 20 ml of RPMI1640 medium at 37° C. under 5% $CO_2$ for 4 days. The human hepatocyte growth factor activity in the culture supernatant was 340 units/ml when measured using the growth of NFS60 cells as the index. On the other hand, in the culture supernatant which was obtained in the same manner except that a vector in which the cDNA of said human hepatocyte growth factor was inserted in the reverse direction and introduced in COS-1 cells, no human hepatocyte growth factor activity was observed.

(7) Expression of human hepatocyte growth factor gene derived from normal fibroblasts in Chinese hamster CHO cells:

The CHO clone DUKXB11 cells (provided by Dr. Chasin of Columbia University), a dihydrofolic acid reductase (DHFR) defective strain of Chinese hamster CHO cells, were cultured overnight in an alpha-MEM (Gibco) medium supplemented with 10% fetal calf serum and nucleic acids at a concentration of $1 \times 10^5$ per well of a 12-well plate.

1 microgram of pSRalphaFDF-1 and 0.1 microgram of pAdD26SV(A)-3 (Scahill, Proc. Natl. Acad. Sci. U.S.A., 80, 4654–4658;, 1983) were mixed and introduced into the above-mentioned CHO cells using a transfection kit by Pharmacia and the cells were cultured for 18 hours. Then, the cell culture was diluted 20 times and incubated for 10 days in an alpha-MEM (Gibco) without nucleic acid and supplemented with 10% fetal calf serum and transformants were obtained.

From the cell strains thus obtained, strains which exhibited high hepatocyte growth factor activity in the culture supernatant were selected and the cells of the selected strains were cultured in an alpha-MEM (Gibco) without nucleic acid and supplemented with 50 nM methotrexate and 10% fetal calf serum; and thus a clone having a high hepatocyte growth factor productivity was obtained and named CHO-6-23-2. The production of human hepatocyte growth factor derived from normal fibroblasts by these cloned cells was 3500 units/ml/2 days when measured using NFS60 cells proliferation assay as the index.

Example 4

A recombinant human hepatocyte growth factor derived from normal fibroblasts was purified from the culture supernatant of the human hepatocyte growth factor-producing monkey COS-1 cells obtained in Example 3 (6).

(1) Salting-out with ammonium sulfate:

5265 g of ammonium sulfate were gradually added to 13.5 liters of the COS-1 cell culture supernatant and dissolved and then the solution was allowed to stand at 4° C. overnight. The precipitate was collected by centrifugation at 6500 rpm for 20 minutes and was dissolved in a 20 mM tris-HCl buffer solution (pH 8.0). The solution was thoroughly dialyzed against the same buffer solution to prepare a concentrated solution by ammonium sulfate.

Figure 4:
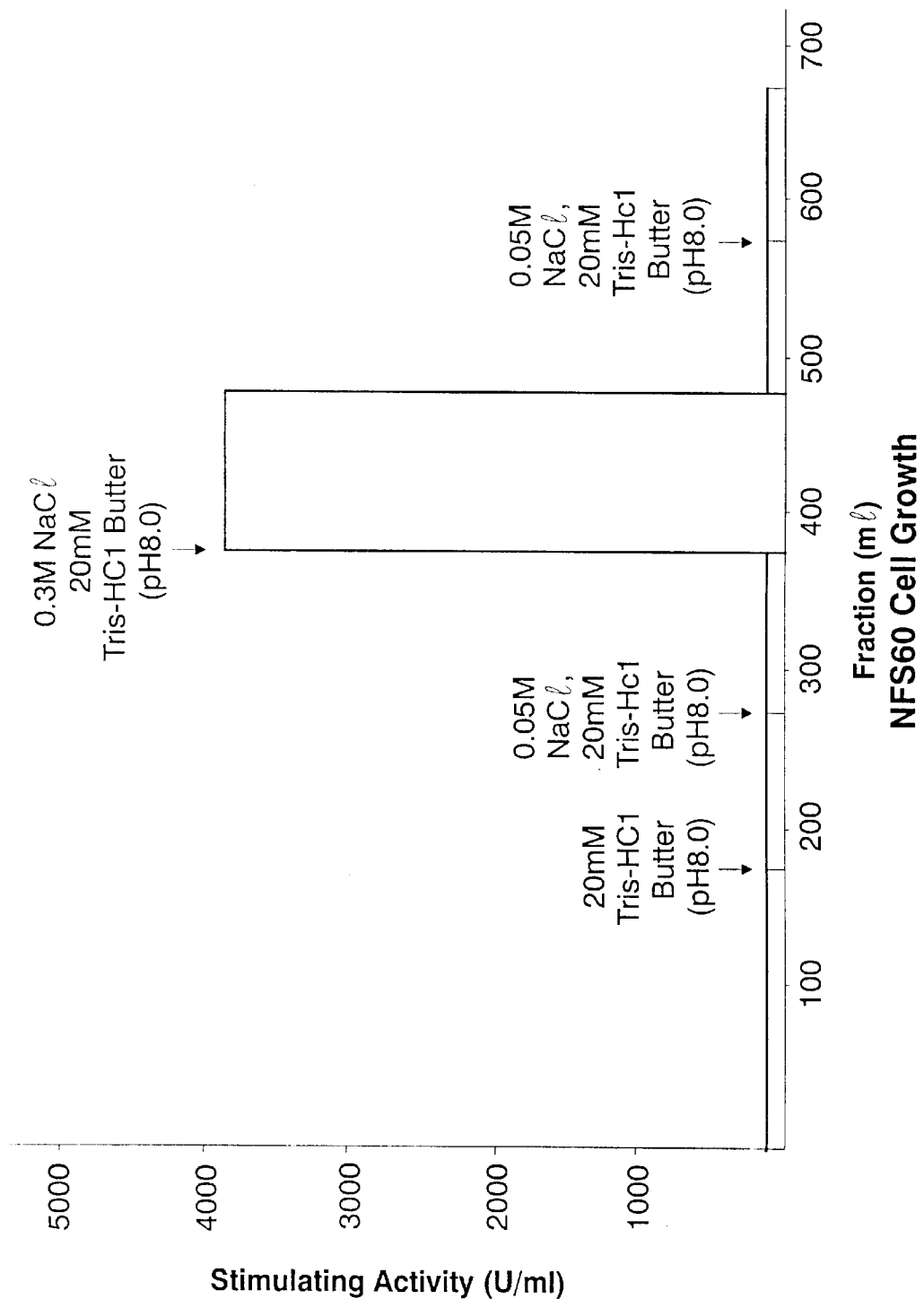
FIG. 4 illustrates the relationships between HGF activity and fractions of a DEAE Sephacel eluent obtained from the culture supernatant of human normal fibroblast hepatocyte growth factor producing monkey COS-1 cells which are obtained in Example 3(6).

(2) Anion exchange chromatography:

The concentrated, ammonium sulfate treated solution obtained in the above-mentioned (1) was added to 10 ml of DEAE Sephacel (Pharmacia) which had been equilibrated with a 20 mM tris-HCl buffer solution (pH 8.0). Unadsorbed substances were washed with a 20 mM Tris-HCl buffer solution (pH 8.0) and then adsorbed substances were eluted by adding in order 100 ml portions of 20 mM tris-HCl buffer solution (pH 8.9) containing NaCl in concentrations of 0.05 M, 0.3 M or 0.5 M. The chromatogram pattern is illustrated in FIG. 4. Fractions showing the NFS60 cell proliferating activity were collected to make a DEAE Sephacel eluate.

Figure 5:
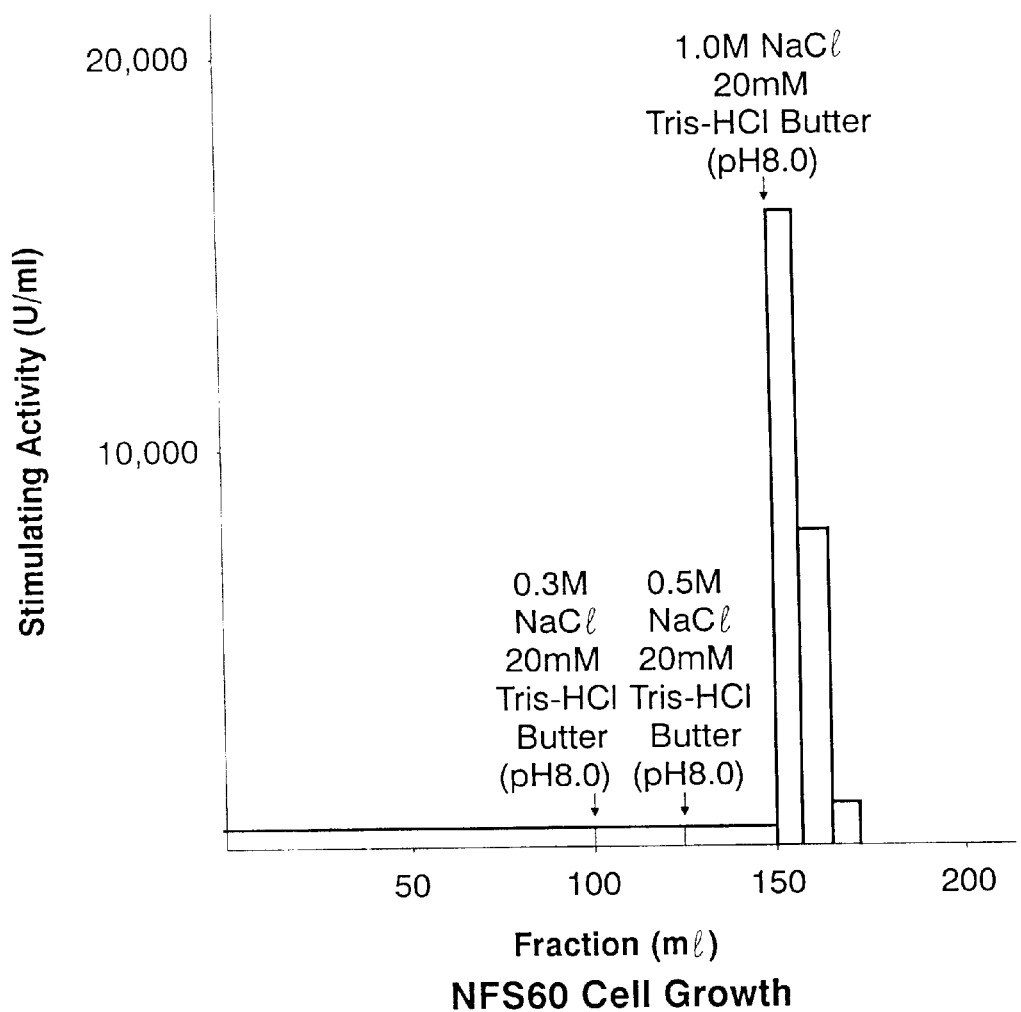
FIG. 5 illustrates the relationships between HGF activity and fractions of a heparin eluent of heparin-Sepharose chromatography of a culture supernatant of human normal fibroblast hepatocyte growth factor producing monkey COS-1 cells which are obtained in Example 3(6).

(3) Heparin-Sepharose CL-6B chromatography:

The DEAE Sephacel eluate was added to 2ml of heparin-Sepharose CL-6B (Pharmacia) which had been equilibrated with a 20 mM tris-HCl buffer solution containing 0.3 M NaCl (pH 8.0). After thoroughly washing with a 20 mM tris-HCl buffer solution containing 0.3 M and then with the same buffer containing 0.5 M NaCl, elution was carried out with a 20 mM tris-HCl buffer solution containing 1 M NaCl (pH 8.0). The chromatogram pattern is illustrated in FIG. 5. Fractions having the NFA60 cell proliferating activity were collected to make a heparin eluate.

Figure 6:
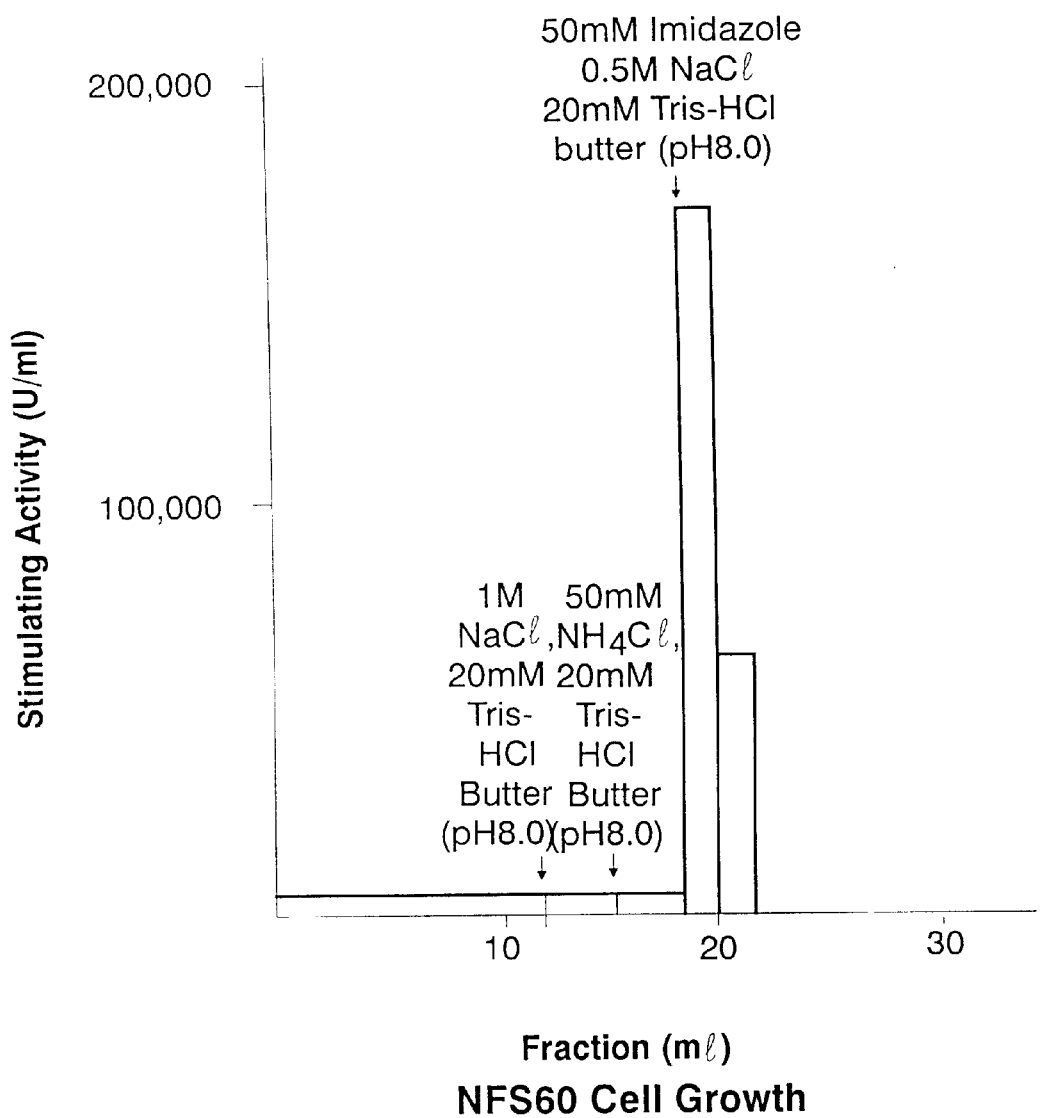
FIG. 6 illustrates the relationships between HGF activity and fractions of a zinc eluent of zinc chelate affinity chromatography of the culture supernatant of human normal fibroblast hepatocyte growth factor producing monkey COS-1 cells which are obtained in Example 3(6).

(4) Zinc chelate affinity chromatography:

0.3 ml of chelating Sepharose 6B (Pharmacia) was packed in a column, a 0.5% aqueous zinc chloride solution was added to the column and the column was washed with a 20 mM tris-HCl solution (pH 8.0) to prepare a column for zinc chelate affinity chromatography. 12 ml of a heparin eluate was added to the column and the column was washed with a 20 mM tris-HCl buffer solution containing 1 M NaCl (pH 8.0). Furthermore, the column was washed with a 20 mM tris-HCl buffer solution containing 50 mM $NH_4Cl$ (pH 8.0) and then elution was carried out with a 20 mM tris-HCl buffer solution containing 50 mM imidazole and 0.5 M NaCl. The elution pattern is illustrated in FIG. 6. Fractions having the NFS60 cell proliferating activity were collected to make a zinc eluate. The yield of the purified recombinant-type hepatocyte growth factor was about 750 micrograms and recovery of the activity from the ammonium sulfate treated concentrate was about 44%.

Figure 7:
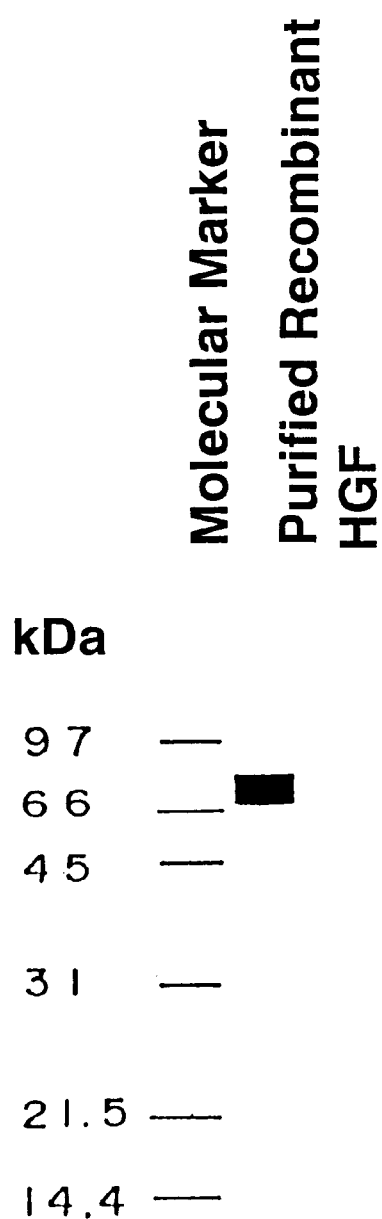
FIG. 7 is a SDS-polyacrylamide gel electrophoresis pattern of recombinant-type human HGF obtained by the purification process as described in Example 4, under non-reducing conditions.
Figure 8:
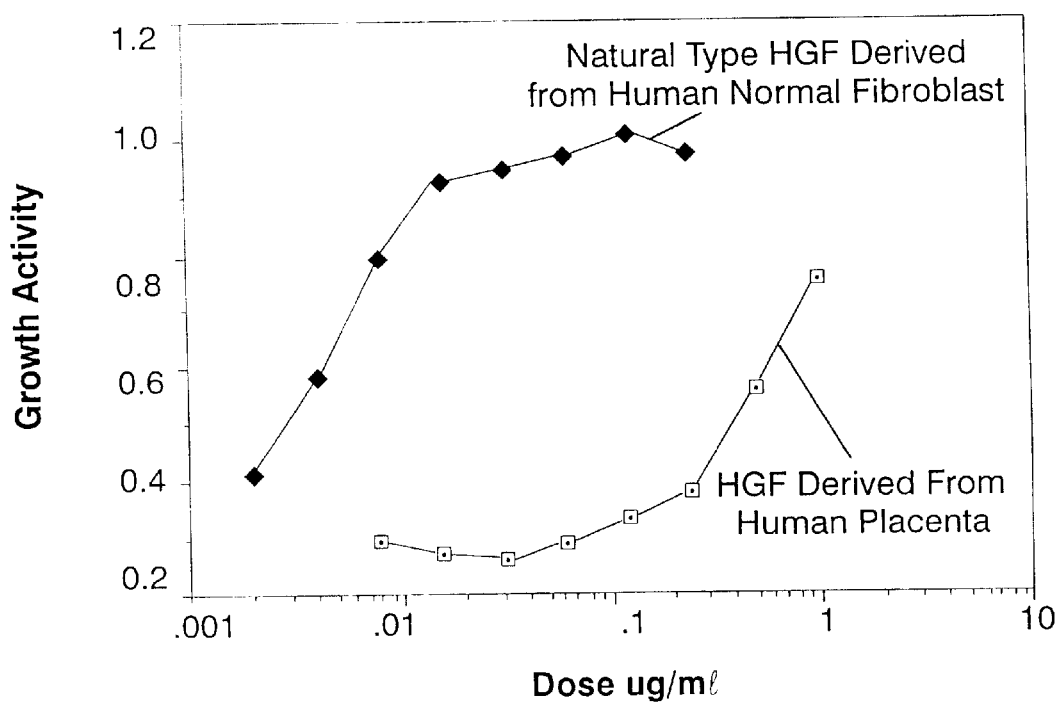
FIG. 8 illustrates NFS60 cell proliferating activity of HGF derived from human placenta and purified HGF derived from fibroblasts.

(5) SDS polyacrylamide gel electrophoresis:

The recombinant-type hepatocyte growth factor prepared by the process described above was applied to SDS-polyacrylamide electrophoresis (4–20% gel) under non-reducing conditions. The recombinant-type hepatocyte growth factor exhibited a single band at a molecular weight between 66,000 and 85,000 under non-reducing conditions. Results are shown in FIG. 7.

Example 5

A recombinant-type human hepatocyte growth factor derived from normal fibroblasts was purified from a culture supernatant of human hepatocyte growth factor-producing chinese hamster CHO recombinant cell strain CHO-6-23-2 obtained in Example 3 (7).

(1) Cation exchange chromatography:

25 ml of a CHO-6-23-2 cell culture fluid was thoroughly dialyzed with a 20 mM tris-HCl buffer solution (pH 6.8) and the dialyzate was added to 0.5 ml of CM-Sephadex (Pharmacia) which had been equilibrated with a 20 mM tris-HCl buffer solution (pH 6.8). After washing with a 20 mM Tris-HCl buffer solution (pH 6.8), the elution was carried out with a 20 mM tris-HCl buffer solution (pH 6.8) containing 0.5 M NaCl. Fractions showing the NFS60 cell proliferating activity were collected to make a CM-Sephadex eluate.

(2) Heparin-Sepharose CL-6B chromatography:

The CM-Sephadex eluate was added to 0.1 ml of heparin-Sepharose CL-6B which had been equilibrated with a 20 mM tris-HCl buffer solution containing 0.5 M NaCl (pH 8.0). After washing with a 20 mM tris-HCl buffer solution containing 0.5 M Nacl, elution was carried out with a 20 mM tris-HCl buffer solution containing 1 M NaCl (pH 8.0). Fractions having the NFA60 cell proliferating activity were collected to make a heparin eluate fraction.

(3) Zinc chelate affinity chromatography:

0.1 ml of chelating Sepharose 6B (Pharmacia) was packed into a column, a 0.5% aqueous zinc chloride solution was added to the column and the column was washed with a 20 mM tris-HCl solution (pH 8.0) to prepare a column for zinc chelate affinity choromatography. The heparin eluate was added to the column and the column was washed with a 20 mM tris-HCl buffer solution containing 1 M NaCl (pH 8.0). Furthermore, the column was washed with a 20 mm tris-HCl buffer solution containing 50 mM $NH_4Cl$ (pH 8.0), and then elution was carried out with a 20 mM tris-HCl buffer solution containing 50 mM imidazole and 0.5 M NaCl. Fractions having the NFS60 cell proliferating activity were collected to make a zinc eluate.

(4) SDS polyacrylamide gel electrophoresis:

The recombinant-type hepatocyte growth factor prepared by the process described above was applied to SDS-polyacrylamide electrophoresis (4–20% gel) under non-reducing conditions; the gel was stained by a silver staining method. The recombinant-type hepatocyte growth factor exhibited a single band at a molecular weight between 66,000 and 85,000 under non-reducing conditions.

Example 6

Measurement of proliferating activity on murine immature myeloblasts (NFS60):

Cell proliferation was measured as follows according to the MTT Assay method (T. Mosman, J. Immunological Methods, 65, 55–63, 1983):.

A 50 microliter aliquot of a culture medium solution (10% FBS-RPM1640) was placed into each well of a 96-well microplate, a 50 microliter aliquot of a solution containing the natural-type hepatocyte growth factor (natural-type human HGF) derived from human normal fibroblasts purified in Example 1 was added to the medium and then a two-step dilution was carried out. A 50 microliter aliquot of $2 \times 10^5$ cells/ml suspension of NFS60 cells was placed in each well and then the plate was cultured at 37° C. for 2 days in a $CO_2$ gas incubator.

Subsequently, a 10 microliter aliquot of MTT reagent [prepared by dissolving 3-(4,5-dimethylthiazol-2-yl)-2,5-diphenyltetrazonium bromide in PBS at 5 mg/ml] was added to each well and the plate was cultured at 37° C. for 5 hours in a $CO_2$ incubator. 150 microliters of 0.04 N hydrochloric acid-added isopropanol was herein added to extract pigment and optical density at 590 nm was determined using an immuno reader.

The natural-type hepatocyte growth factor derived from human normal fibroblasts, purified in Example 1 (a natural-type human HGF), showed activity at a dilution rate where the OD 590 value was 50% of that for the maximum response.

Example 7

Determination of DNA synthesis stimulating activity on mature rat primary culture hepatocytes:

Mature rat hepatocytes were isolated and purified by the method of Seglen (Seglen, P. O., Methods in Cell Biology, 13, 29–83, 1976).

Freshly prepared hepatocytes ($1 \times 10^5$) were added to a medium of the following composition and the total volume was made into 1 ml; a medium containing MEM (Gibco), 100 mM insulin (Sigma), 50 micrograms/ml gentamycin (Sigma), 5% calf serum (Gibco) and HGF was dispensed in a collagen-coated 35-mm plastic petri-dish (Falcon). Incubation was carried out in an incubator in an atmosphere of 7% $CO_2$ and 90% humidity at 37° C. for 4 hours. After incubation, the medium was changed with a fresh serum-free MEM medium containing 5 microCi/ml[$^3$H] thymidine. The incubation was continued for another 45 hours under the same conditions as described above. The cultured petri-dish was washed 6 times with 0.9% NaCl. The cells were dissolved in 1.5 ml of 0.33 N NaOH and then the resultant solution was transferred into a test tube in ice water.

0.5 ml of 40% trichloroacetic acid dissolved in 1.2 N hydrochloric acid was added to the solution and the resultant precipitate was isolated by centrifugation at 2,000 rpm for 10 minutes. The precipitate thus obtained was dissolved in 0.5 ml of 0.33 N NaOH and a 0.3 ml portion of the solution was placed into a scintillation vial and then 0.5 ml of Aquasol (New England Nuclear) and 0.4 ml of 40% trichloroacetic acid in a 1.2 N hydrochloric acid solution was added to this vial. Uptake of [$^3$H] thymidine incorporation was measured by a scintillation counter. Hepatocyte growth factor derived human normal fibroblasts purified in Example 1 (natural-type human HGF) exhibited the activity.

Example 8

Measuremet of growth stimulating activity on hemopoietic stem cells using human normal bone marrow cells:

2 to 3 ml of heparin-added normal human bone marrow blood was sampled and allowed to stand in the presence of silica at 37° C. for 30 minutes and then non-phagocytic monocytes were isolated by Ficoll-Paque (Pharmacia) gravity centrifugation. After washing, adhesive cells were removed using a 10-cm plastic petri-dish and the remaining non-phagocytic, non-adhesive monocytes (NPNAMNC) were allowed to suspend in an alpha-medium (Flow Labs).

Culture was carried out by a methyl cellulose method which is a modified method of Iscove et al. (Iscove, N. N. et al., J. Cell Physiol., 83, 309–320, 1974). The above-mentioned NPNAMNC ($4\times10^4$ cells) were added to a serum free medium having the following composition and the total volume of the medium was made into 1 ml. The medium contained alpha-medium, 0.8% methyl cellulose (Shin-etsu Kagaku), 0.1% crystallized deionized bovine serum albumin (Sigma), 300 micrograms/ml Fe-saturated human transferrin (Sigma), 40 micrograms/ml soy bean lecithin (Sigma), 24 microgram/ml cholesterol (Nakarai Chemical), $5\times10^5$ M 2-mercaptoethanol and was dispensed into a 35-mm Lux culture dish (Miles Labs) with samples added to the medium. Incubation was carried out in an incubator in an atmosphere of 5% $CO_2$ and with 100% humidity at 37° C. for 18 days. Then colonies were observed under an inverted microscope and the number of colonies was counted.

Results are shown in Table 2.

TABLE 2

Hemopoietic stem cells growth stimulating activity of natural-type human HGF on human normal bone marrow cells

| Natural-type HGF added | Number of colony formed/4 × $10^4$ NPNAMNC | | | | |
|---|---|---|---|---|---|
| | Blast | CFU-GM | CFU-G | Macrophage | Total |
| None | 10 | 19 | 5 | 6 | 40 |
| 1 ng/ml | 6 | 26 | 7 | 1 | 40 |
| 10 ng/ml | 17 | 38 | 9 | 1 | 65 |
| $10^2$ ng/ml | 13 | 38 | 9 | 4 | 64 |
| $10^3$ ng/ml | 15 | 30 | 4 | 5 | 54 |

Example 9

Measurement of growth promoting activity on hemopoietic stem cells using murine bone marrow cells:

150 mg/kg of 5-fluorouracil was injected intravenously to a BDF1 female mouse and after 48 hours bone marrow cells were taken from the thigh bone.

Culture was carried out by a methyl cellulose method which is a modified method of Iscove et al. $5\times10^4$ bone marrow cells were added to a serum-free medium having the following composition and the total volume of the culture was made into 1 ml. The medium contained alpha-medium, 0.9% methyl cellulose, 1% crystallized deionized bovine serum albumin, 300 micrograms/ml Fe-saturated human transferrin, 160 micrograms/ml soy bean lectin (Sigma), 96 micrograms/ml cholesterol (Nakarai Chemical), $10^{-4}$ M 2-mercaptoethanol and samples or various hemopoietic factors added; the medium thus prepared was dispensed into 35-mm Lux culture dishes. Each hemopoietic factors was added at the following concentration: 200 u/ml for rmuIL-3 (Cosmo Bio Co., Ltd.) and 20 u/ml for rmuIL-7 (Cosmo Bio Co., Ltd.).

Incubation was carried out in an incubator in an atmosphere of 5% $CO_2$ and 100 % humidity at 37° C. After incubation for 17 days, colonies were observed under an inverted microscope and the number of colonies was counted.

Results for the natural-type hepatocyte growth factor derived from human normal fibroblasts are shown in

TABLE 3

Hemopoietic stem cells growth stimulating activity of natural-type human HGF on 5FU-treated murine bone marrow cells

| Natural-type HGF added | Colonies /5 × $10^4$ 5FU-resistant bone marrow cells | | | | |
|---|---|---|---|---|---|
| | Blast | CFU-GM | CFU-G | Macrophage | Total |
| None | 0 | 0 | 0 | 0 | 0 |
| $10^2$ ng/ml | 0 | 0 | 0 | 0 | 0 |
| + IL-3 | 0 | 1 | 0 | 0 | 1 |
| + IL-3 + IL-7 | 8 | 8 | 5 | 2 | 23 |
| $10^3$ ng/ml | 12 | 14 | 0 | 6 | 32 |

IL-3: 200 micro/ml
IL-7: 20 micro/ml

Example 10

Measurement of hepatocyte growth promoting activity of recombinant-type and natural-type HGF derived from human normal fibroblasts:

Hepatoparenchyma cells were isolated from a 4-week-old Wister rat by a collagenase flux method. The hepatoparenchyma cells thus obtained were suspended in an Williams E medium containing 5% fetal calf serum, $1\times10^9$ M insulin and $1\times10^{-9}$ dexamethasone at a concentration of $10^5$ cells/ml. 0.5 ml portions of the cell suspension thus prepared were dispensed into a collagen-coated 23-well multiplate and the plate was incubated at 37° C. for 20 hours in the presence of 5% $CO_2$. Subsequently, the medium was exchanged by a fresh Williams E medium containing $1\times10^{-9}$ insulin and $1\times10^{-9}$ M dexamethasone and at the same time a specified amount of samples were added. Incubation was continued for another 23 hours and then 0.5 microCi per well of $^{125}$I deoxyuridine was added and incubation was continued for another 7 hours. The cells thus obtained were washed twice with PBS and then treated with a cold 10% trichloroacetic acid aqueous solution. The cells were solubilized with 0.5 ml per well of 1N NaOH and the radioactivity of the solution was measured by a gamma counter. A portion of the sample after the radioactivity measurement was taken and measured for the amount of protein by the Lawry method. Radioactivity incorporated in the hepatoparenchyma cells when various samples were added was measured and was converted to per 1 microgram of hepatoparenchyma cell protein to give DNA synthesis activity (cpm/microgram protein).

Results are shown in Table 4.

TABLE 4

Hepatocyte proliferating activity of recombinant-type and natural-type HGF derived from human normal fibroblasts

| | Concentration | DNA synthesis in hepatoparenchyma cells (cpm/microgram cell protein/7h) |
|---|---|---|
| Natural-type | 100 ng/ml | 131 ± 3.6 |
| human HGF | 10 ng/ml | 78 ± 2.5 |
| | 1 ng/ml | 44 ± 4.0 |
| | 100 pg/ml | 22 ± 1.0 |
| | 10 pg/ml | 30 ± 1.0 |
| Recombinant-type | 100 ng/ml | 104 ± 3.6 |
| human HGF | 10 ng/ml | 60 ± 6.1 |
| | 1 ng/ml | 26 ± 0.6 |
| | 100 pg/ml | 24 ± 1.5 |
| | 10 pg/ml | 26 ± 4.2 |
| Epithelial cell | 50 ng/ml | 60 ± 3.0 |
| growth factor | 10 ng/ml | 58 ± 5.9 |
| | 2 ng/ml | 40 ± 6.7 |
| Insulin | 100 nM | 54 ± 3.0 |
| | 10 nM | 43 ± 1.5 |
| | 1 nM | 32 ± 4.0 |
| Insulin + Epithelial cell growth factor | 100 nM 20 ng/ml | 100 ± 3.5 |
| Natural-type Human HGF + Insulin | 50 ng/ml 100 nM | 137 ± 4.4 |
| Recombinant-type human HGF + Insulin | 50 ng/ml 100 nM | 118 ± 3.5 |
| Natural-type human HGF + Epithelial cell | 50 ng/ml 20 ng/ml | 140 ± 8.9 |
| Recombinant-type human HGF + Epithelial cell growth factor | 50 ng/ml 20 ng/ml | 110 ± 5.1 |
| Natural-type human HGF + Insulin + Epithelial cell growth factor | 50 ng/ml 100 nM 20 ng/ml | 153 ± 7.5 |
| Recombinant-type human HGF + Insulin + Epithelial cell growth factor | 50 ng/ml 100 nM 20 ng/ml | 138 ± 10.7 |

Both natural-type HGF which was purified in Example 1 and derived from human normal fibroblasts and recombinant type HGF which was purified in Example 4 and derived from COS cells exhibited DNA synthesis activity at 10 ng/ml and in the presence of insulin and/or epithelial cell growth factor, DNA synthesis activity on hepatoparenchyma cells was enhanced.

Example 11

Colony formation stimulating activity of recombinant-type and natural-type HGFs derived from human normal fibroblasts using normal murine bone marrow cells:

Bone marrow cells were taken from the thigh bone of a BDF1 mouse and according to the conventional method (Metcalf Clonal Culture of Hemopoietic Cells: Techniques and Applications, Elsevier, Amsterdam), $2 \times 10^4$ of the bone marrow cells were suspended in 1 ml of alpha-MEM medium containing $1 \times 10^{-4}$ M 2-mercaptoethanol, 20% fetal calf serum and HGF sample in various concentrations; incubation was carried out at 37° C. for 7 days in the presence of 5% $CO_2$ and then colonies formed were observed under an inverted microscope and counted.

Results are shown in Table 5.

TABLE 5

Colony assay using untreated bone marrow cells

| | Number of GM clusters |
|---|---|
| Natural-type HGF derived from human normal fibroblasts (Unit/ml) | |
| 0 | 0 |
| 25 | 6.3 ± 2.9 |
| 100 | 9.8 ± 4.3 |
| 400 | 7.0 ± 1.8 |
| 1600 | 0.8 ± 1.0 |
| Recombinant-type HGF derived from human normal fibroblasts (Unit/ml) | |
| 0 | 2.3 ± 3.3 |
| 25 | 9.8 ± 5.5 |
| 100 | 20.0 ± 5.5 |
| 400 | 15.0 ± 3.6 |
| 1600 | 15.8 ± 1.3 |

Example 12

Measurement of NFS60 cell proliferating activity of hepatocyte growth factor derived from human placenta:

NFS60 cell proliferating activity of hepatocyte growth factor derived from human placenta (Becton Dickinson Labware) and natural-type hepatocyte growth factor derived from human normal fibroblasts, which was purified in Example 1, was measured by the method described in Example 6. Results are shown in Table 8.

In the same manner, NFS60 cell proliferating activity of the recombinant-type hepatocyte growth factor derived from human normal hepatocytes (Nature, 342, 440–443, 1989) and a recombinant-type hepatocyte growth factor derived from fibroblast M426 of human fetal lung (Proc. Natl. Acad. Sci. U.S.A., 88, 415–419, 1991) can be measured by the method described in Example 6.

POSSIBILITY OF INDUSTRIAL USE

A hepatocyte growth factor has an activity to support the growth of immature myeloblast derived from mice. Furthermore, since the factor supports the growth of hemopoietic stem cells in an evaluation system using human bone marrow cells and murine bone marrow cells, it can be used as a stem cell augmenting agent having said hepatocyte growth factor as an active component for treatment of bone marrow suppression (for example, after the use of anti-cancer agents or after bone marrow transplantation), for treatment of bone marrow malfunctions (for example, hypoplastic anemia), or for in vitro growth of peripheral blood stem cells and bone marrow stem cells. Furthermore, since the hemopoietic stem cell augmenting agent in the present invention eventually promotes the growth of not only various blood cells but also osteoclasts which are progeny of hemopoietic stem cells, it is appropriately used as a therapeutic agent for osteoporosis or the like.

What is claimed is:

1. A process for promoting the proliferation and differentiation of hemopoietic stem cells comprising contacting immature bone marrow cells with a hepatocyte growth factor.

2. A process for promoting the proliferation and differentiation of hemopoietic stem cells comprising contacting pluripotent hemopoietic stem cells with a hepatocyte growth factor.

3. A process for promoting the proliferation and differentiation of hemopoietic stem cells comprising contacting human bone marrow cells with a hepatocyte growth factor.

4. The process of any one of claims 1–3 further comprising contacting said cells with IL-3.

5. The process of any one of claims 1–3 further comprising contacting said cells with IL-3 and IL-7.

6. The process of any one of claims 1–3 wherein said hepatocyte growth factor is encoded by the DNA sequence of SEQ ID NO. 2.

7. The process of any one of claims 1–3 wherein said hepatocyte growth factor is encoded by the amino acid sequence of SEQ ID NO. 2.

8. A composition comprising hepatocyte growth factor and IL-3.

9. A composition comprising hepatocyte growth factor, IL-3 and IL-7.

* * * * *